(12) United States Patent
Wong et al.

(10) Patent No.: US 11,214,586 B2
(45) Date of Patent: Jan. 4, 2022

(54) RHODAMINE TRIPLET STATE COMPLEX AND PREPARATION AND PHOTODYNAMIC THERAPY (PDT) STUDY THEREOF

(71) Applicants: SOUTHERN UNIVERSITY OF SCIENCE AND TECHNOLOGY, Shenzhen (CN); SHENZHEN INSTITUTES OF ADVANCED TECHNOLOGY CHINESE ACADEMY OF SCIENCES, Shenzhen (CN)

(72) Inventors: Keith Man Chung Wong, Shenzhen (CN); Chuangjun Liu, Shenzhen (CN); Ping Gong, Shenzhen (CN); Lihua Zhou, Shenzhen (CN); Lintao Cai, Shenzhen (CN)

(73) Assignees: SOUTHERN UNIVERSITY OF SCIENCE AND TECHNOLOGY, Shenzhen (CN); SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 0 days.

(21) Appl. No.: 16/767,786

(22) PCT Filed: Aug. 16, 2018

(86) PCT No.: PCT/CN2018/100896
§ 371 (c)(1),
(2) Date: May 28, 2020

(87) PCT Pub. No.: WO2020/034164
PCT Pub. Date: Feb. 20, 2020

(65) Prior Publication Data
US 2020/0361972 A1 Nov. 19, 2020

(51) Int. Cl.
*C07F 15/00* (2006.01)
*C07F 13/00* (2006.01)
*A61P 35/00* (2006.01)

(52) U.S. Cl.
CPC ............ *C07F 15/004* (2013.01); *A61P 35/00* (2018.01); *C07F 13/00* (2013.01); *C07F 15/008* (2013.01);
(Continued)

(58) Field of Classification Search
None
See application file for complete search history.

(56) References Cited

PUBLICATIONS

Huang ("Room-Temperature Long-Lived 3IL Excited State of Rhodamine in an NAN PtII Bis(acetylide) Complex with Intense Visible-Light Absorption" Eur. J. Inorg. Chem. 2011, p. 4527-4533) (Year: 2011).*

(Continued)

*Primary Examiner* — Amy C Bonaparte
(74) *Attorney, Agent, or Firm* — Jenkins, Wilson, Taylor & Hunt, P.A.

(57) ABSTRACT

Through the use of a rhodamine appended chelate, a versatile strategy has been demonstrated to generate mitochondria-targeting photosensitizers via the incorporation of variety of luminescent transition metal systems. The generation of triplet excited state of rhodamine moiety endows the complexes with mitochondria-targeting photosensitizing ability to form singlet oxygen ($^1O_2$) for use as photodynamic therapy (PDT) agent. The combination of rhodamine organic dye and luminescent transition metal centers in such hybrid systems exhibits the synergistic merits, including low dark cytotoxicity, selective tumor cell uptake, high molar absorptivity for low-energy excitation in the visible region, and high photostability.

9 Claims, 25 Drawing Sheets

(52) U.S. Cl.
CPC ...... *C07F 15/0033* (2013.01); *C07F 15/0046* (2013.01); *C07F 15/0073* (2013.01); *C07F 15/0093* (2013.01)

(56) References Cited

PUBLICATIONS

Zhang ("Photophysical, ion-sensing and biological properties of rhodamine-containing transition metal complexes", Coordination Chemistry Reviews, 2020, 416, p. 213336 (1-19)) (Year: 2020).*
Dolmans et al., "Photodynamic therapy for cancer". Nat Rev Cancer 3, 2003, 380-387.
Oleinick et al., "The Role of Apoptosis in Response to Photodynamic Therapy: What, Where, Why, and How," Photochem. Photobiol. Sci. 2002, 1, pp. 1-21.
Lee et al., "New energy transfer dyes for DNA sequencing," Nucleic Acids Research, vol. 25, No. 14, 1997, pp. 2816-2822.
Davis et al., "Mitochondrial and Plasma Membrane Potentials Cause Unusual Accumulation and Retention of Rhodamine 123 by Human Breast Adenocarcinoma-derived MCF-7 Cells*," J. Biol. Chem. vol. 260, No. 25, 1985.
Moan et al., "The Photodegradation of Porphyrins in Cells Can Be Used to Estimate the Lifetime of Singlet Oxygen," Photochem. Photobiol. vol. 53, No. 4, 1991, pp. 549-553.
Kessel et al., "Photodynamic therapy: A mitochondrial inducer of apoptosis," Cell Death and Differentiation, 6, 1999, pp. 28-35.
Dougherty et al., "Photodynamic therapy." Journal of the National Cancer Institute, vol. 90,12, 1998, pp. 889-905.
Hill et al., "Selenorhodamine photosensitizers for photodynamic therapy of P-glycoprotein-expressing cancer cells," Journal of Medicinal Chemistry, 57, 2014, pp. 8622-8634.
Leonard et al., "A Selenopyrylium Photosensitizer for Photodynamic Therapy Related in Structure to the Antitumor Agent AA1 with Potent in Vivo Activity and No Long-Term Skin Photosensitization," Journal of Medicinal Chemistry, vol. 43, No. 23, 2000, pp. 4488-4498.
Tong et al., "Mononuclear ruthenium polypyridine complexes that catalyze water oxidation," Chemical Science, 7, 2016, pp. 6591-6603.
Andreev et al., "Mechanism and uses of a membrane peptide that targets tumors and other acidic tissues in vivo," Proc. Natl. Acad. Sci. U.S.A. 104, 2007, pp. 7893-7898.
Xuan et al., "Synthesis and in Vitro Studies of a Series of Carborane-Containing Boron Dipyrromethenes (BODIPYs)," J. Med. Chem. 59, 2016, pp. 2109-2117.
Wong et al., "Bichromophoric rhodamine-rhenium(I) and -iridium(III) sensory system: Synthesis, characterizations, photophysical and selective metal ions binding studies." Polyhedron. vol. 86, Jul. 14, 2014 (Jul. 14, 2014), pp. 133-140.
International Search Report and Written Opinion for Application No. PCT/CN2018/100896 dated May 20, 2019.

* cited by examiner (a)

(b)

(a)

(b)

(a)

(b)

(a)

(b)

(a)

(b)

(a)

(b)

RHODAMINE TRIPLET STATE COMPLEX AND PREPARATION AND PHOTODYNAMIC THERAPY (PDT) STUDY THEREOF

TECHNICAL FIELD

The invention relates to photodynamic therapy field, particularly to a mitochondria-targeting photosensitizer from the combination of a transition metal and rhodamine tethered bipyridine.

BACKGROUND

Photodynamic therapy (PDT), which is regarded as a less invasive tumor treatment, is a clinically approved technique to eradicate a variety of tumor cells by using a photosensitizer, molecular oxygen, and light.[1-3] Upon photo-excitation, the photosensitizer with a triplet excited state from an intersystem crossing (ISC) pathway is able to generate reactive oxygen species (ROS), such as singlet oxygen ($^1O_2$), which is cytotoxic to tumor cells and immediately induces apoptosis.[2,3] In order to fulfil the criteria of a large molar extinction coefficient, high ISC efficiency and good photostability, there has been much interest in the development of ideal photosensitizers.[2,3] On the other hand, the exploration of photosensitizers, with high tumor selectivity also represents a major challenge as it is one of the major limitations of PDT.

Rhodamine, one of the most common organic dyes, has been widely applied in chemosensing[4] and biomolecule labelling,[5] in view of its great photo-stability, lower excitation and emission energies, large molar extinction coefficient and high fluorescence quantum yield, as well as good water solubility.[6] Since tumor cells with higher mitochondria activity are typically showing higher net negative charge than normal cells,[7] the cationic rhodamine can be attracted and accumulated onto the mitochondria,[8] facilitating its rapid migration towards the diseased organelle.[9] In order to circumvent the limitations caused by the short lifetime (<0.04 μs) and small subcellular diffusion radius in body tissue (<0.02 μm) of $^1O_2$,[10] localization of the photosensitizer close to the organelle, that can effectively trigger cell death, is also crucial. ROS in mitochondria is considered to cause cell death which is related to apoptosis.[2,11] The fascinating features of selectivity for tumor cells and subcellular localization in mitochondria from rhodamine has prompted us to develop rhodamine-based photosensitizers for PDT.[8,12] Since the rhodamine itself is not able to efficiently yield a triplet state and hence $^1O_2$ upon photo-irradiation, generation of rhodamine triplet state for application in PDT is relatively rare. In order to facilitate its triplet state formation, one approach is to incorporate a heavy atom into the rhodamine molecule, such as attaching Br or I on the xanthene framework, or replacing O atom by S, Se or Te atom.[8,12] Their relatively high dark toxicity, poor hydrophilicity, low photostability and/or tedious synthetic procedures, however, have limited practical application and generalization.

The photo-functional properties of transition metals complexes, such as those of Ru(II), Re(I). Ir(III) and Pt(II), have been extensively studied, including phosphorescence, photocatalysis, PDT, and triplet-triplet annihilation (TTA).[13-18] Most of them are related to their triplet excited states, resulting from efficient ISC[13d,18] associated with the heavy atom effect. However, the moderate molar absorption coefficient in the visible spectral region and the relatively high cytotoxicity are significant drawbacks for their applications in PDT. Recently, spectroscopic studies of rhodamine-containing Pt(II) complexes showed the accessibility of the rhodamine triplet state.[19] However, the use of dithiolate or alkynyl group on rhodamine as ligating site limits the choice of transition metals.

SUMMARY

Herein, we report a versatile strategy to generate rhodamine triplet state as mitochondria-targeting photosensitizers for efficient PDT. The principle behind this is to make use of rhodamine tethered bipyridine as the chelating ligand, bpy-Rho, which can readily coordinate to a variety of transition metal centers. In order to demonstrate the generalization of our strategy, a series of complexes of Re(I), Ir(III), Rh(III) and Pt(II) with this ligand (M-Rho) were synthesized (FIG. 1). Their PDT effects were evaluated to verify our "proof-of-principle" about the synergism of combining rhodamine and transition metals for the design of mitochondria-targeting photosensitizers. The synthesis and characterization of the ligand bpy-Rho and the complexes M-Rho are shown in the Supporting Information (Scheme 1 and FIGS. 7-11) and the X-ray crystal structure of Re-Rho is depicted in FIG. 12.

The first aspect of the invention provides a complex from the combination of a transition metal and rhodamine tethered bipyridine of Formula I

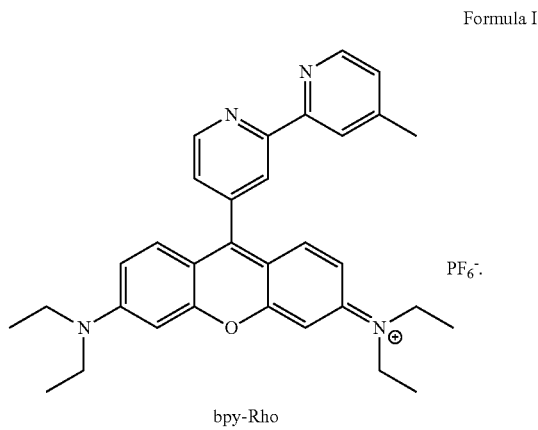

Formula I bpy-Rho

In an embodiment, the transition metal is selected from the group consisting of Re(I), Ir(III), Rh(III) and Pt(II).

In a preferred embodiment, the complex is selected from the group consisting of:

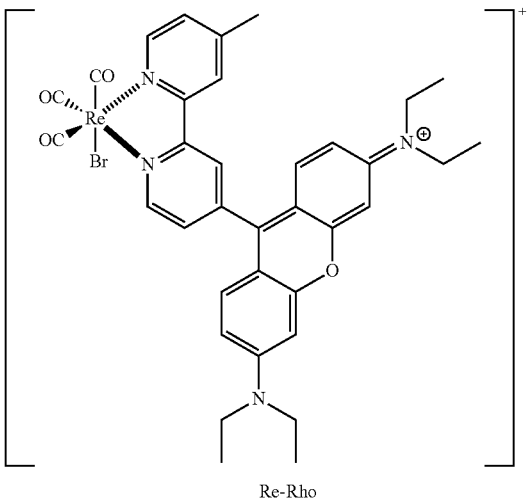

Re-Rho

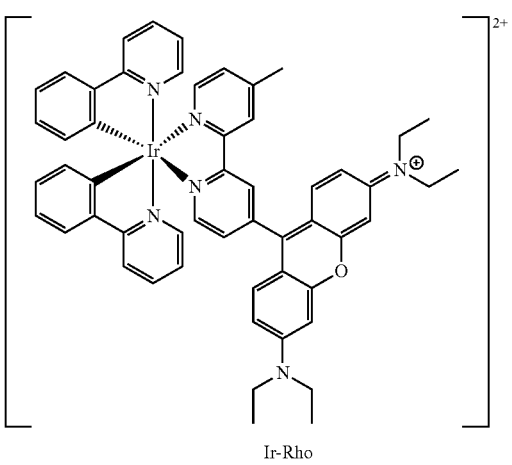

Ir-Rho

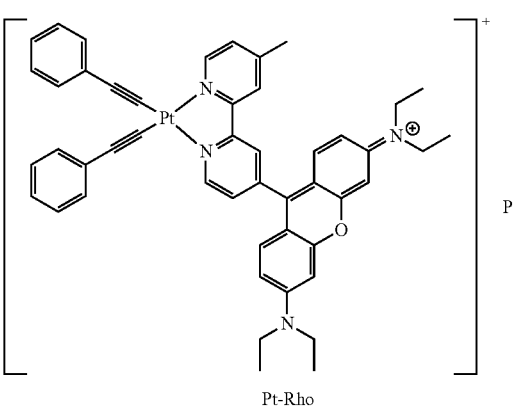

Pt-Rho and

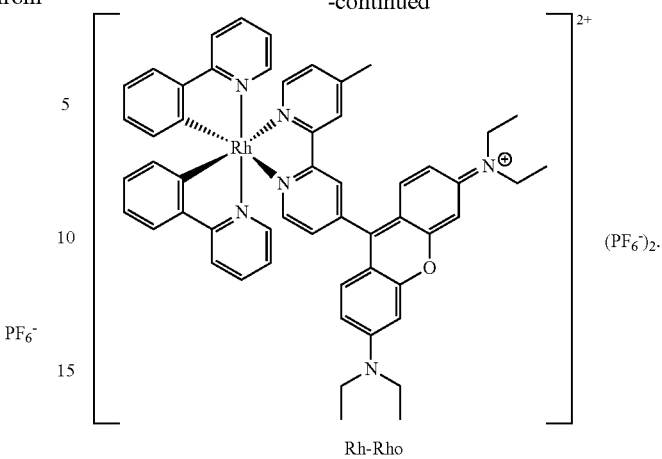

Rh-Rho

The second aspect of the invention provides a preparation method of the complex of the invention, comprising the following steps:

(1) preparing bpy-Rho of Formula I according to the following strategy at the presence of (i) $SeO_2$, 1,4-dioxane, reflux; (ii) 3-(diethylamino)phenol, $CH_3COOH$, ρ-TsOH, chloranil;

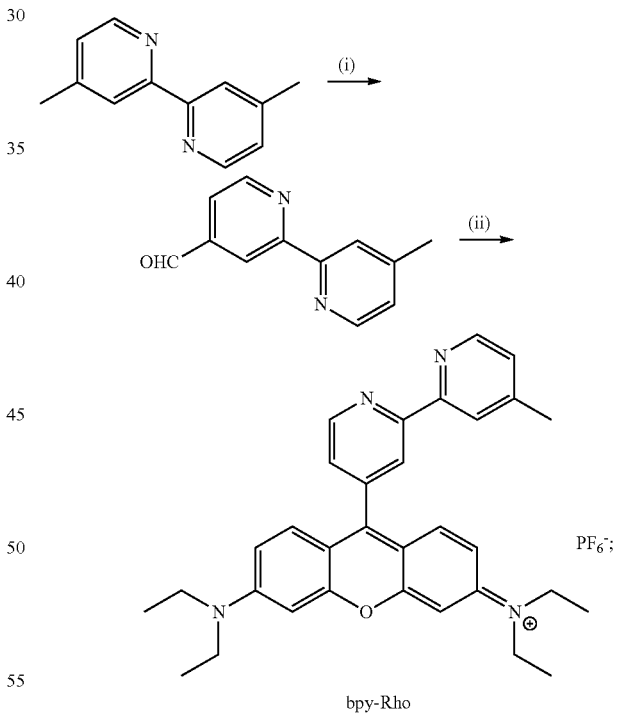

bpy-Rho and (2) preparing the complex by chelating the bpy-Rh with a transition metal.

In an embodiment, the transition metal is selected from the group consisting of Re(I), Ir(III), Rh(III) and Pt(II).

The third aspect of the invention provides use of the complex of the invention as a mitochondria-targeting photosensitizer.

In an embodiment, the mitochondria-targeting photosensitizer is used in photodynamic therapy and/or selective tumor cellular uptake.

DETAILED DESCRIPTION

Figure 13:
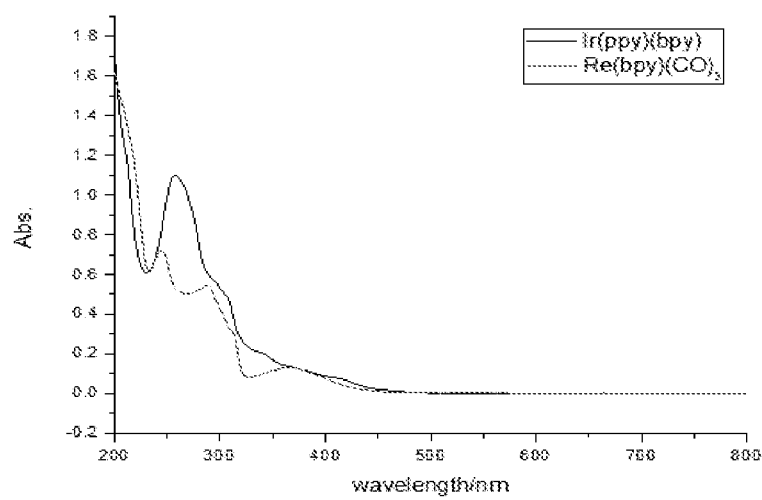
FIG. 13 shows UV/Vis absorption spectra of Ir(ppy)$_2$(bpy) and Re(bpy)(CO)$_3$Br in MeCN at 298 K.

All the complexes exhibit an intense low-energy absorption at 574 nm in CH3CN, attributed to the intraligand (IL) π-π* transition of the rhodamine unit (FIG. 2a) since no such absorption was observed in rhodamine-free analogues of Re-Rho and Ir-Rho (FIG. 13). The photophysical data are summarized in Table 1. The ligand bpy-Rho shows the characteristic rhodamine absorption at 564 nm, which was red-shifted upon the incorporation of transition metal centers.

Figure 1:
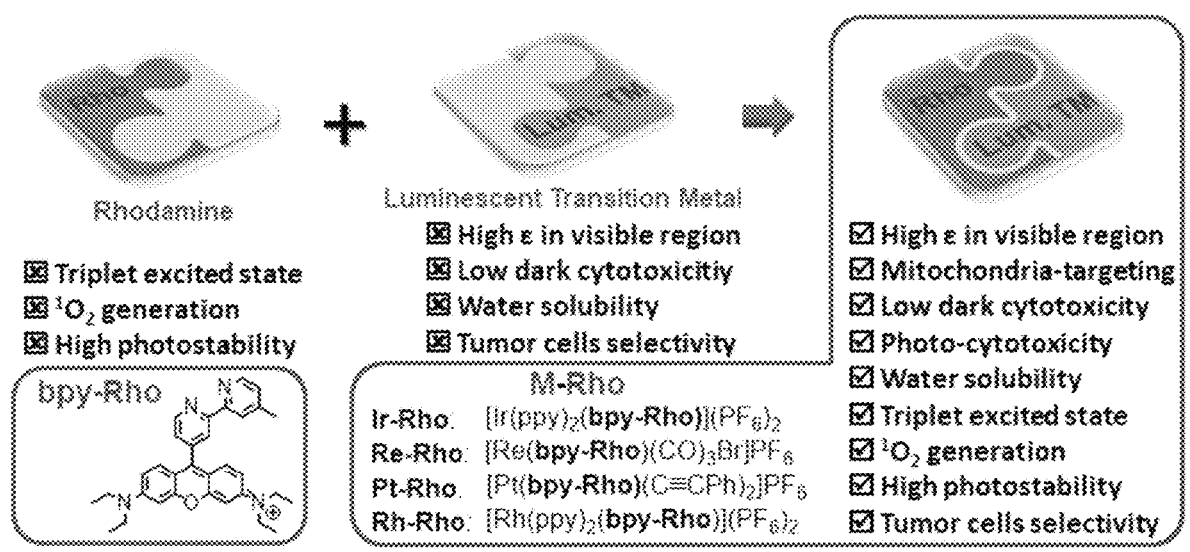
FIG. 1 shows synergism from rhodamine appended metal complexes, M-Rho.
Figure 2:
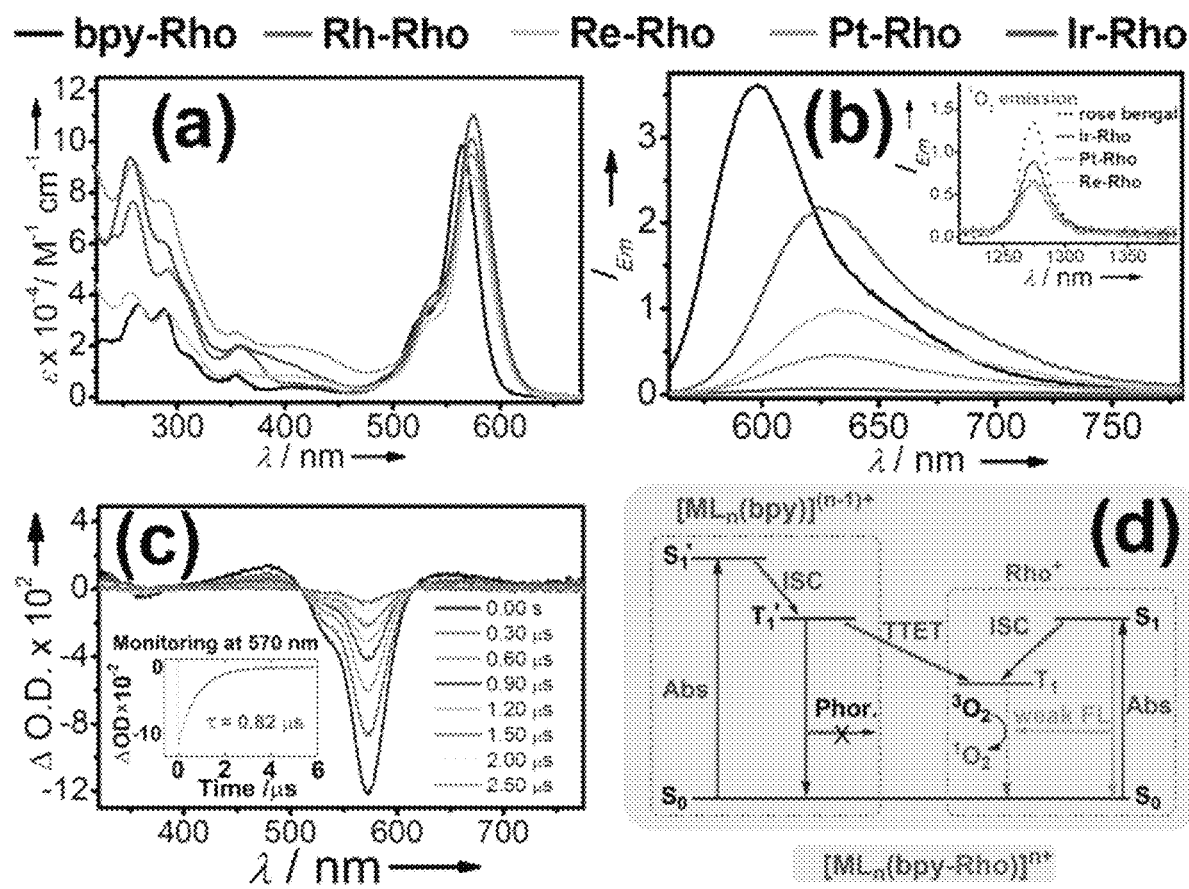
FIG. 2 shows (a) UV/Vis absorption and (b) fluorescence spectra of bpy-Rho and M-Rho in CH3CN (ex. at 550 nm with abs.=0.6). (c) Transient absorption difference spectrum of Ir-Rho in CH3CN. (d) Proposed energy diagram for M-Rho for illustration of emission quenching. Inset of (b) 1O2 emission spectra.
Figure 14:
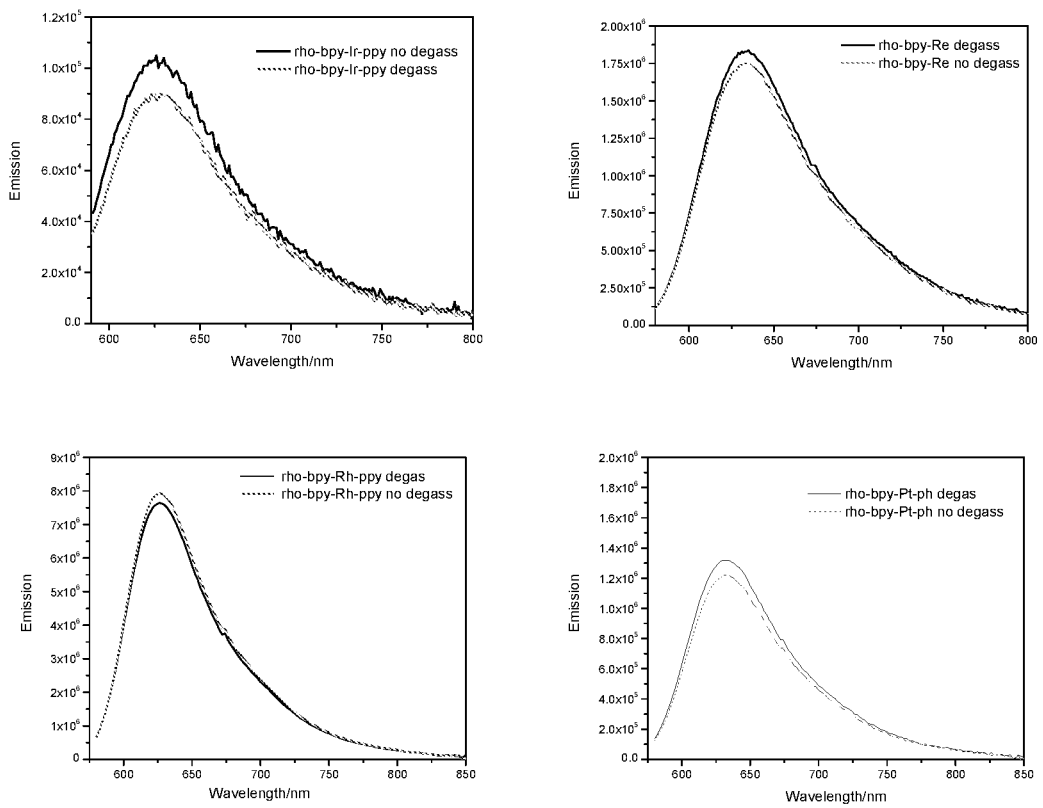
FIG. 14 shows the oxygen dependency of the emission of M-Rho.
Figure 15:
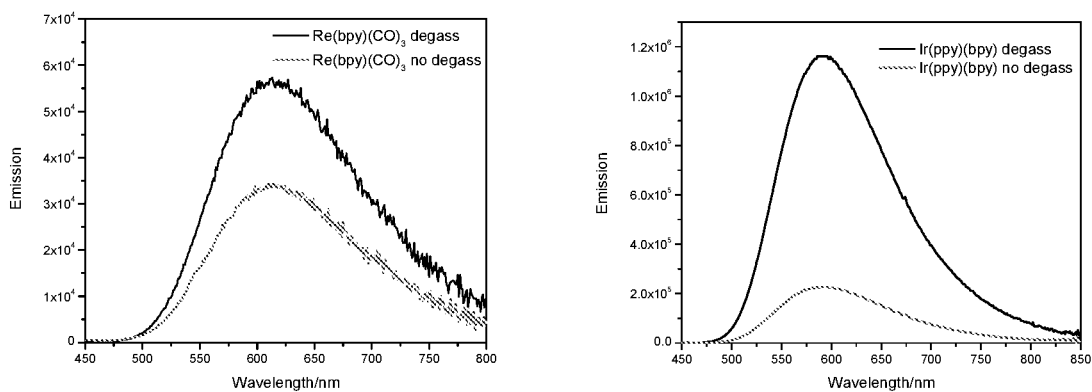
FIG. 15 shows the oxygen dependency of the emission of model metal complexes.
Figure 16:
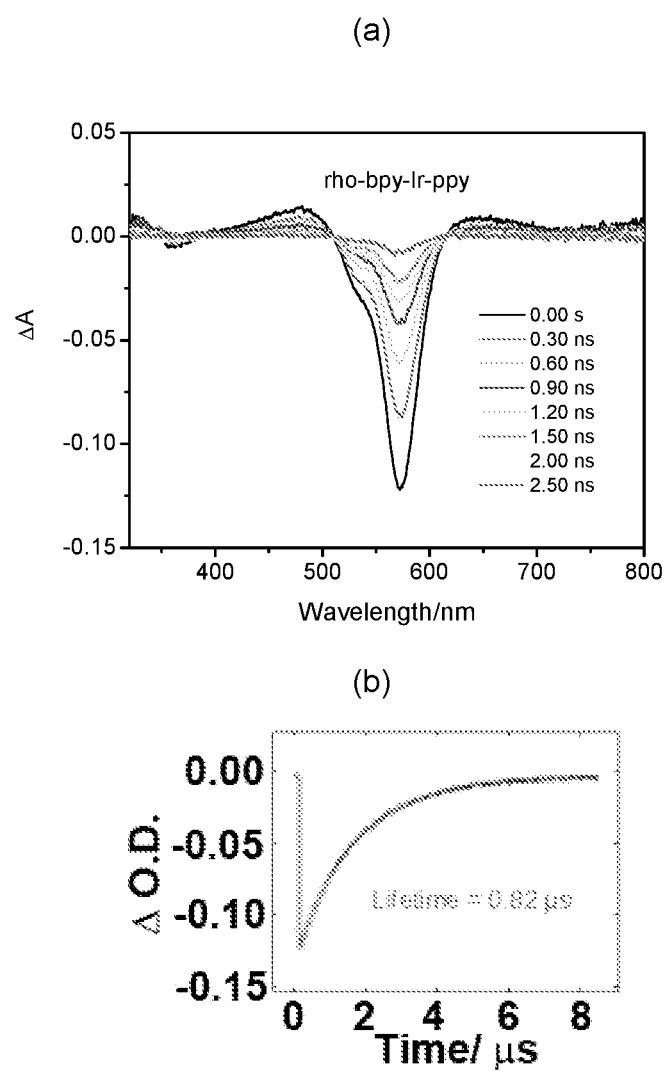
FIG. 16 shows transient absorption difference spectra of Ir-Rho (top) and decay trace at 575 nm (bottom). The spectra were recorded in deaerated $CH_3CN$; $\lambda_{ex}$=355 nm, 25° C.
Figure 17:
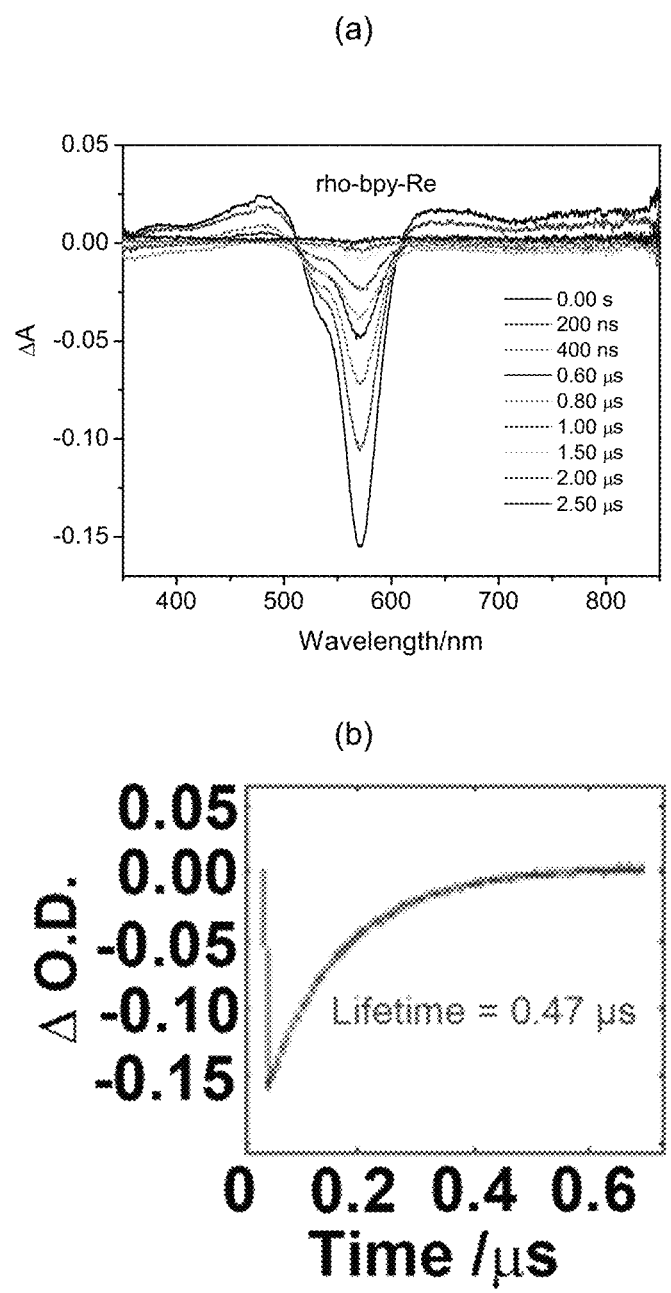
FIG. 17 shows transient absorption difference spectra of Re-Rho (top) and decay trace at 575 nm (bottom). The spectra were recorded in deaerated $CH_3CN$; $\lambda_{ex}$=355 nm, 25° C.
Figure 18:
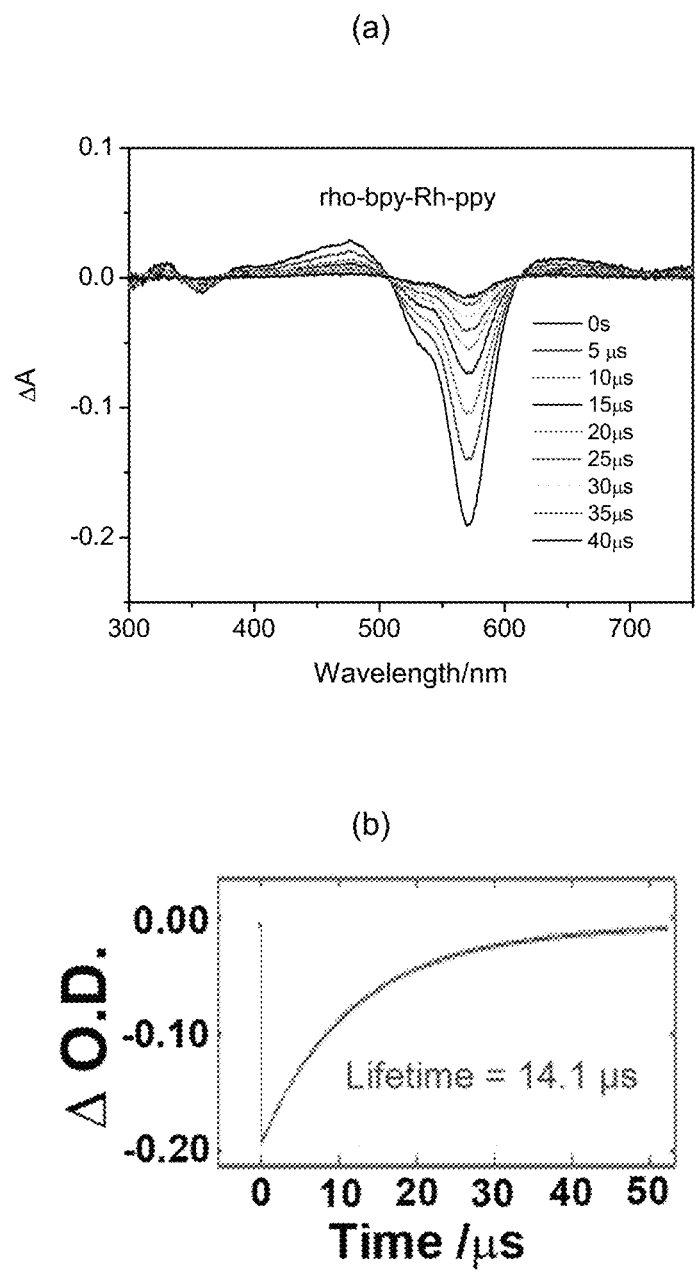
FIG. 18 shows transient absorption difference spectra of Rh-Rho (top) and decay trace at 575 nm (bottom). The spectra were recorded in deaerated $CH_3CN$; $\lambda_{ex}$=355 nm, 25° C.
Figure 19:
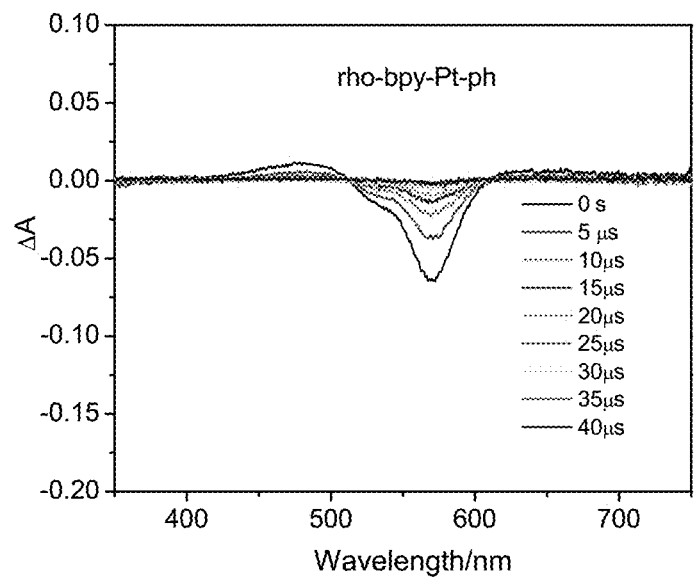
FIG. 19 shows transient absorption difference spectra of Pt-Rho (top) and decay trace at 575 nm (bottom). The spectra were recorded in deaerated $CH_3CN$; $\lambda_{ex}$=355 nm, 25° C.
Figure 19:
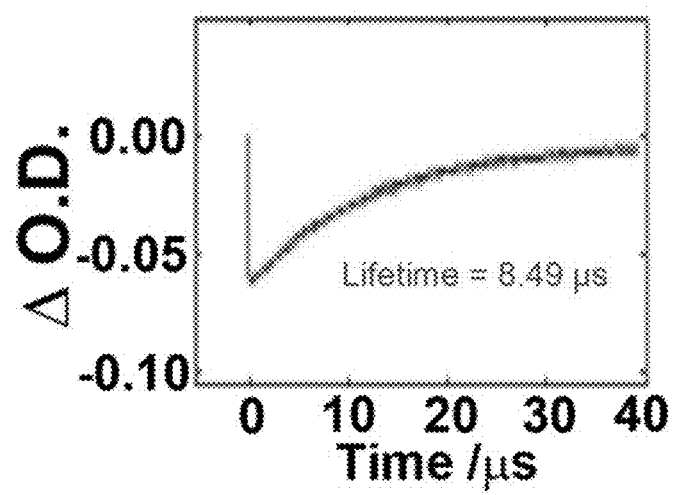

The emission spectrum of bpy-Rho shows intense emission at 598 nm in MeCN with luminescence quantum yield ($\phi_{lum}$) of 0.29, while those of the complexes are found to give emission at around 630 nm with $\phi_{lum}$ of 0.014-0.23 (FIG. 2b and Table 1). In view of the small Stokes shifts and the oxygen insensitivity of the emission intensity (FIG. 14), the emission is assigned as fluorescence originated from the singlet state of rhodamine. Such rhodamine emission in M-Rho is also found to shift to the red, relative to the ligand bpy-Rho. It is noteworthy that their emission intensities are reduced and dependent on the nature of the metal systems (FIG. 2b), with the same absorbance at the excitation wavelength. By comparison to the emission spectra of the rhodamine-free analogues, [Re(bpy)(CO)$_3$Br] and [Ir(ppy)$_2$(bpy)]$^+$ (FIG. 15), such intrinsic phosphorescence of the triplet metal-to-ligand charge transfer ($^3$MLCT) state is essentially quenched in M-Rho upon combination with a rhodamine unit.

Figure 20:
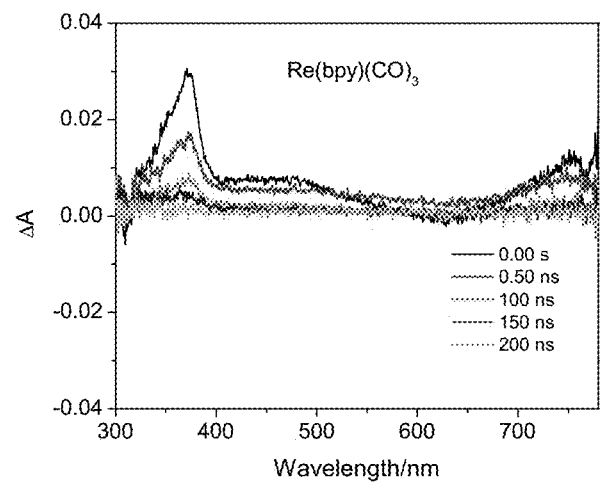
FIG. 20 shows transient absorption difference spectra of Re(bpy)(CO)$_3$Br (top) and decay trace at 374 nm (bottom). The spectra were recorded in deaerated $CH_3CN$; $\lambda_{ex}$=355 nm, 25° C.
Figure 20:
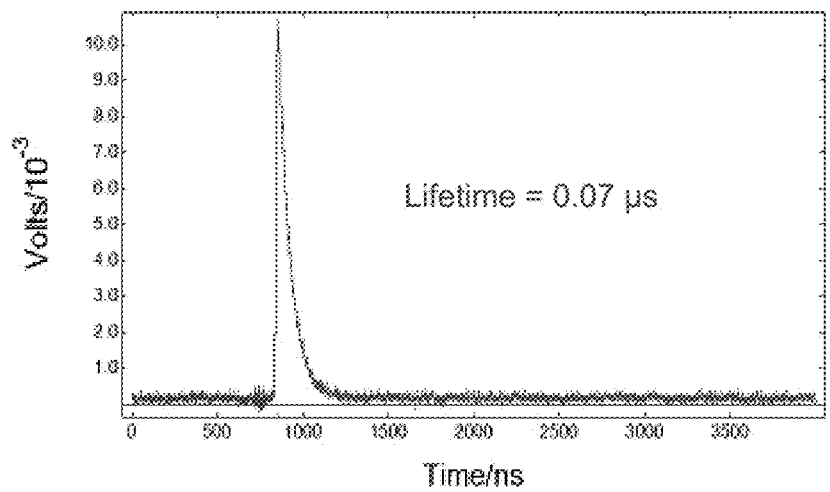
Figure 21:
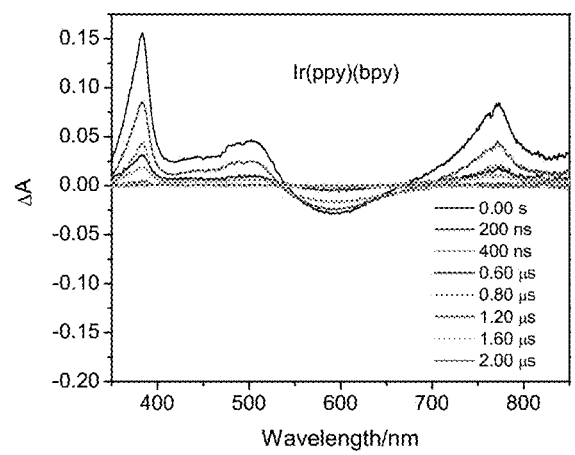
FIG. 21 shows transient absorption difference spectra of Ir(ppy)$_2$(bpy) (top) and decay trace at 770 nm (bottom). The spectra were recorded in deaerated $CH_3CN$; $\lambda_{ex}$=355 nm, 25° C.
Figure 21:
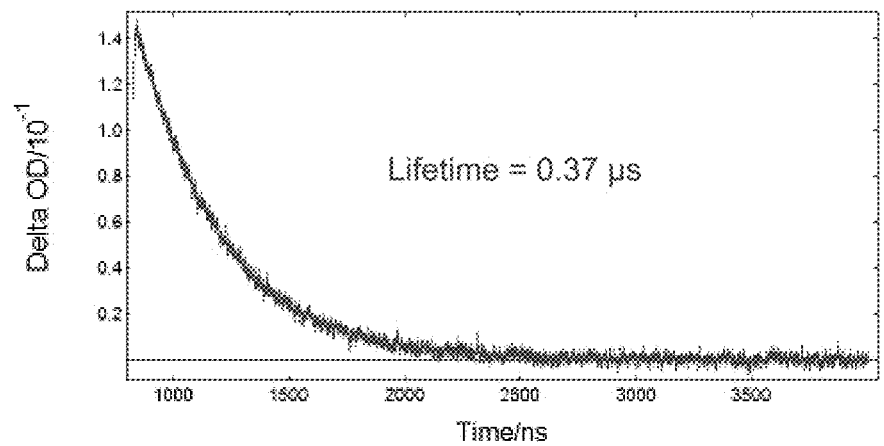
Figure 22:
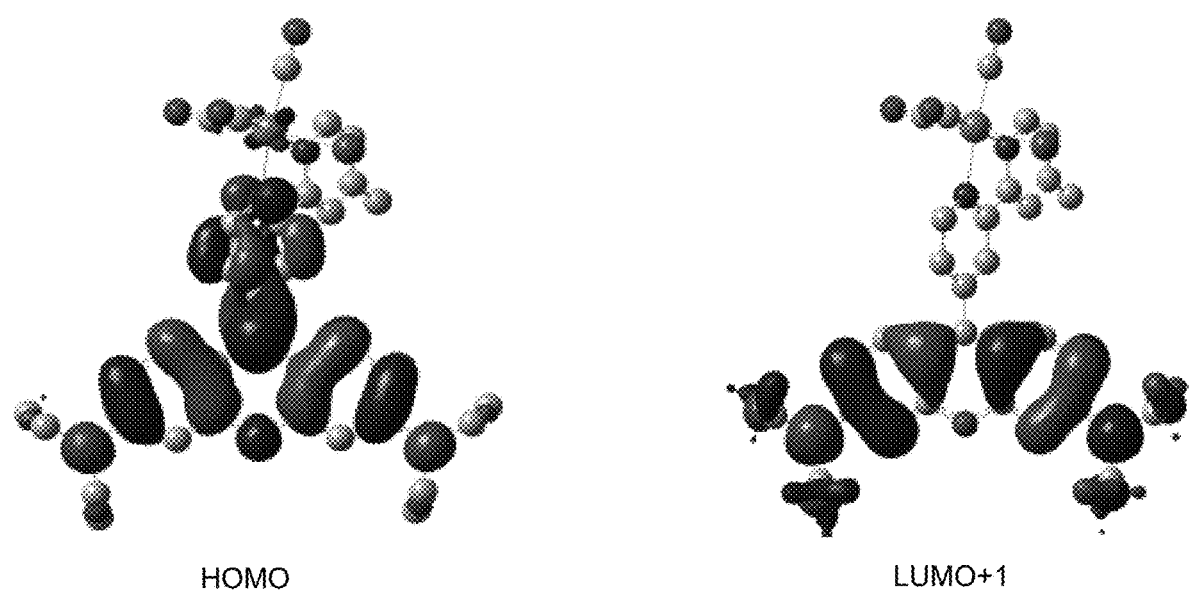
FIG. 22 shows frontier molecular orbitals involved in the T1 excited state of Re-Rho. The calculation was carried out at the B3PW91/6-31++g*/LanL2DZ level with Gaussian 09W.

Nanosecond transient absorption (TA) difference spectroscopy was employed to investigate the triplet excited states of M-Rho (FIG. 2c and FIGS. 16-19). Upon pulsed laser excitation at 355 nm, an intense bleaching signal at 575 nm with lifetime in microsecond range is observed, which is ascribed to the depletion of ground state rhodamine absorption. Such a long-lived excited state should be localized on the rhodamine unit, and is assigned as the $^3$IL excited state of rhodamine in M-Rho. The absorption signal at 610-800 nm is due to the rhodamine $^3$IL excited state absorption. In contrast, no signal from this triplet excited state is detected in bpy-Rho because of the lack of efficient ISC. On the other hand, only the transient absorption signals originating from the corresponding $^3$MLCT excited states are observed in the rhodamine-free analogues (FIGS. 20-21). TDDFT computational study of Re-Rho (with X-ray crystal structure) also confirms that the transition involved in the T$_1$ state is from HOMO to LUMO+1 and both of them are mainly localized on the rhodamine moiety (FIG. 22), suggesting its $^3$IL excited state nature.

Figure 23:
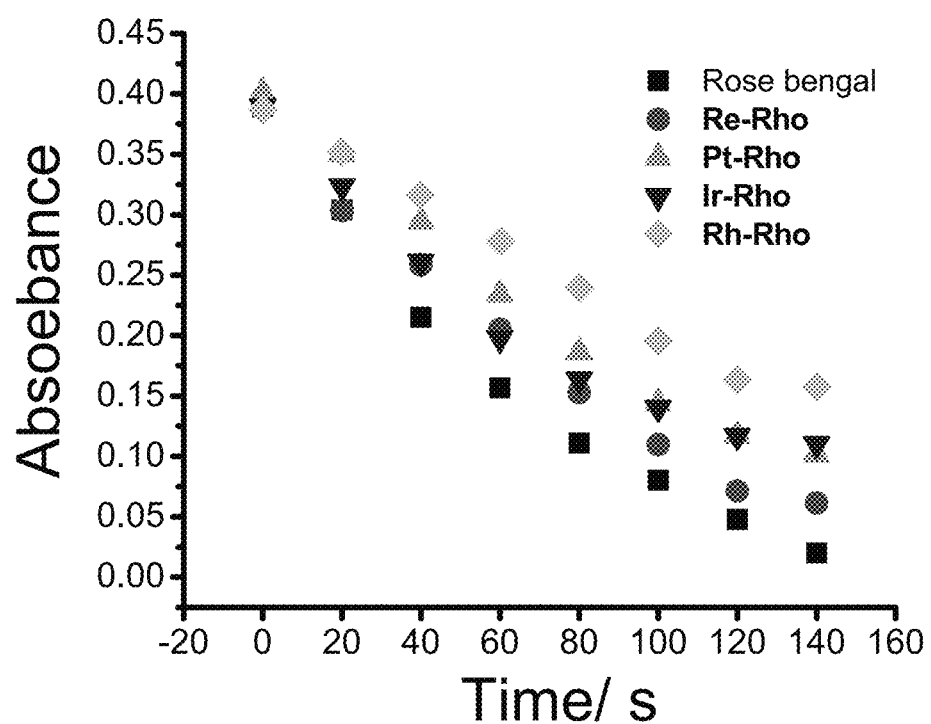
FIG. 23 shows solutions containing 50 µM of DPBF and 5 µM compounds in $CH_2Cl_2$ were stirred open to the air and irradiated with 11 W lamp. Rose Bengal was measured in MeOH.
Figure 24:
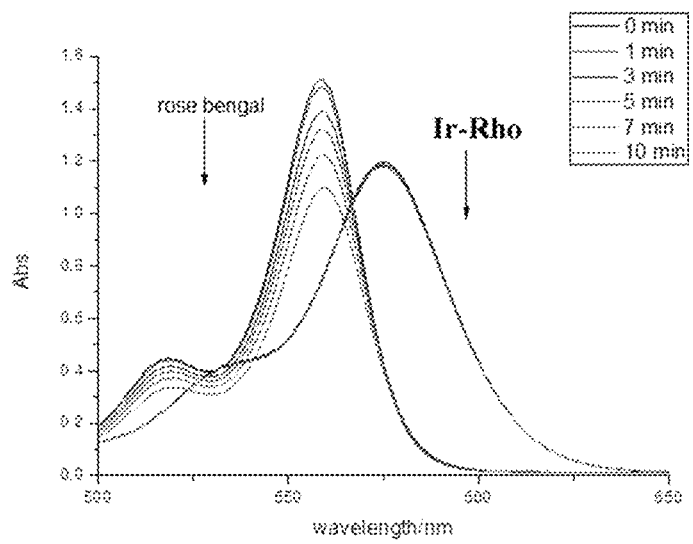
FIG. 24 shows comparison between Ir-Rho and rose Bengal in photostability study under same conditions using 532 nm laser with 336 mW/cm$^2$.

The long-lived triplet excited state of rhodamine is anticipated to interact with molecular oxygen ($^3$O$_2$) to form singlet oxygen ($^1$O$_2$), which is useful for PDT applications. The ability of M-Rho to produce $^1$O$_2$ has been evaluated spectroscopically by the observation of $^1$O$_2$ emission at about 1270 nm (inset of FIG. 2b). Remarkable $^1$O$_2$ emission is observed in Ir-Rho, Re-Rho and Pt-Rho but not for Rh-Rho and bpy-Rho. By monitoring the diminution of the characteristic absorption of the $^1$O$_2$ scavenger 1,3-diphenylisobenzofuran (DPBF) at 410 nm, $^1$O$_2$ generation is also confirmed and the corresponding quantum yields ($\phi_\Delta$) for the complexes are determined (Table 1). In the presence of any M-Rho complex, the DPBF absorbance also shows a remarkable rapid drop at 410 nm upon irradiation with a 11-W lamp (FIG. 23), suggestive of their strong abilities to generate $^1$O$_2$. The rate and quantum yield of $^1$O$_2$ generation are found to vary with different metal systems. Ir-Rho give highest QY while Rh-Rho is the worst photosensitizer for $^1$O$_2$ generation. In contrast, DPBF or bpy-Rho alone shows a negligible decrease in the absorption at 410 nm under identical conditions. These results strongly suggest that the incorporation of various transition metal systems into the rhodamine unit can significantly enhance the ability of $^1$O$_2$ generation, mainly originated from the formation of triplet state (T$_1$) from rhodamine. Compared to the common photosensitizer, rose Bengal, M-Rho are much more photostable as revealed from their negligible absorption spectral change during irradiation (FIG. 24), demonstrating their high resistance to photobleaching and excellent photostability.

TABLE 1

Photophysical parameters of bpy-Rho and M-Rho.

| | $\lambda_{abs}$, nm | $\varepsilon \times 10^4$, M$^{-1}$ cm$^{-1}$ [b] | $\lambda_{em}$, nm [a] | $\Phi_{lum}$ [c] | T$_{T_1}$ μs [d] | $\Phi_\Delta$ [e] |
|---|---|---|---|---|---|---|
| bpy-Rho | 564 | 9.86 | 598 | 0.29 | n.d. | 0.08 |
| Re-Rho | 574 | 7.00 | 631 | 0.093 | 0.47 | 0.59 |
| Ir-Rho | 575 | 8.75 | 629 | 0.014 | 0.82 | 0.62 |
| Pt-Rho | 574 | 7.96 | 631 | 0.062 | 8.49 | 0.57 |
| Rh-Rho | 574 | 8.24 | 629 | 0.23 | 14.1 | 0.37 |

[a] Conc. = 1.0 × 10$^{-6}$M in MeOH.
[b] Molar extinction coefficient at the absorption maxima.
[c] Absolute luminescence quantum yield measured by HAMAMATSU-C11347.
[d] Triplet-state lifetimes, measured by transient absorption in CH$_3$CN.
[e] Singlet oxygen quantum yield, relative to rose bengal ($\Phi_\Delta$ = 0.76).

According to the observation of strong emission in either organic rhodamine dyes or rhodamine-free metal complex analogues, the quenching mechanism upon the combination of two systems is rationalized as shown in the energy diagram (FIG. 2c). Taking Ir-Rho as an example, the phosphorescence from state of [Ir(ppy)$_2$(bpy)]$^+$ is significantly quenched through the efficient triplet-triplet energy transfer (TTET) to the rhodamine triplet state (T$_1$). On the other hand, the disappearance of rhodamine fluorescence is attributed to the population of the rhodamine T$_1$ state from its singlet state, arising from the efficient ISC process upon incorporation of heavy atom iridium (III) metal center. Although no emission can be observed from this T$_1$ state of rhodamine, transient absorption spectroscopy shows the presence of such dark state. Deactivation of T$_1$ can also be achieved by the interaction with molecular oxygen to generate $^1$O$_2$. In principle, the stronger is the fluorescence observed from rhodamine S$_1$, the lower is the efficiency of $^1$O$_2$ generation. The highest luminescence QY observed from rhodamine S$_1$ in Rh-Rho is ascribed to the least efficient ISC process, arising from its smallest spin-orbit coupling (SOC), relative to the third row Re(I), Ir(III) and Pt(II) transition metal systems. Accordingly, less rhodamine triplet state can be generated and the lowest $\phi_\Delta$ value is observed.

Figure 3:
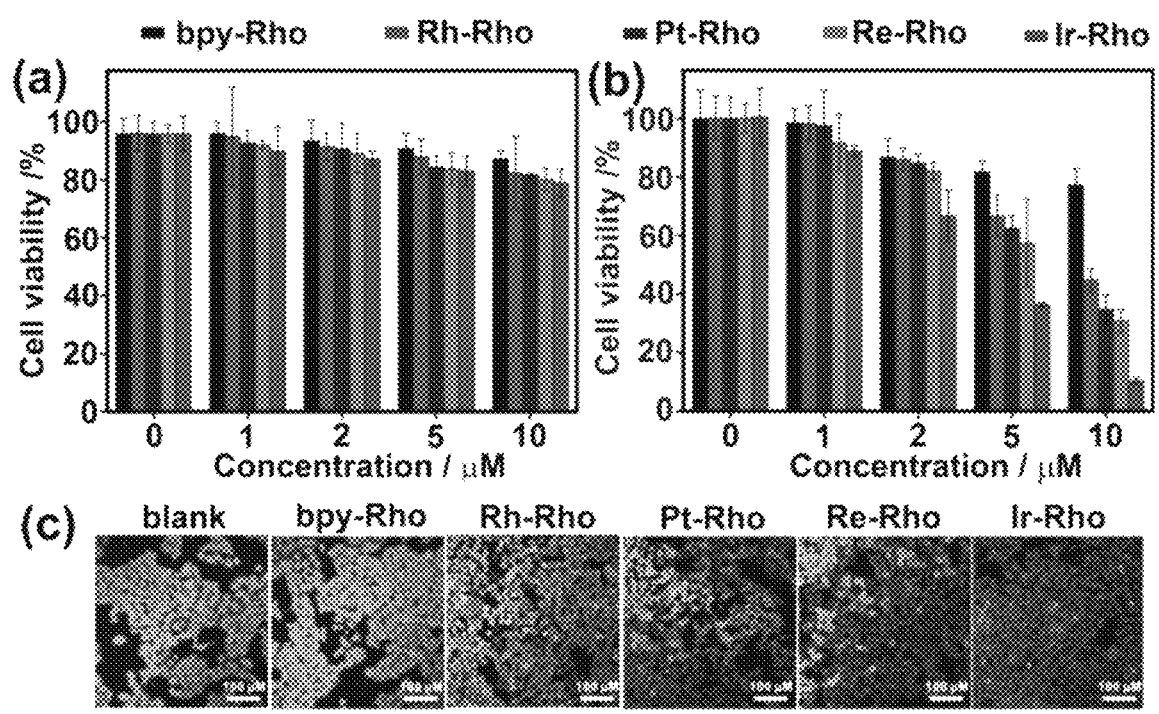
FIG. 3 shows In vitro cell viability of MCF-7 cells treated with different concentrations of bpy-Rho and M-Rho (a) in the dark and (b) after irradiation with 11-W lamp. (c) Fluorescence images of MCF-7 cells treated with blank, bpy-Rho and M-Rho (5 µM) irradiated with 11-W lamp for 30 min. Viable cells were stained green with calcein-AM, and dead cells were stained red with PI. (Scale bar=100 µm).

The in vitro PDT properties of bpy-Rho and M-Rho in MCF-7 cells are then evaluated by CCK-8 assays. Negligible or small change in cell viability is observed without light irradiation (FIG. 3a), suggesting their low cytotoxicity in the dark. It is noteworthy that the dark cytotoxicity of M-Rho is significantly reduced upon coordination with the rhodamine tethered ligand, when compared to the related rhodamine-free transition metal complexes,[13b,16b,20]. Upon irradiation with a 11-W lamp, the cell viability is gradually decreased with increasing concentrations of bpy-Rho and M-Rho (FIG. 3b). Significant cell death is observed for Ir-Rho at the concentration of 10 μM. Simultaneous staining of living and dead cells by green fluorescent calcein-AM and red fluorescent propidium iodide (PI), respectively, further verify their relative PDT efficiencies upon 11-W lamp irradiation (FIG. 3c). Their photo-cytotoxic properties are basically in line with the $^1$O$_2$ generation ability, as indicated by their $^1$O$_2$ emission intensities and $\phi_\Delta$ as well as intracellular and mitochondria-localized ROS yield (vide infra). Among these complexes M-Rho, the best PDT performance is found in Ir-Rho, which shows the strongest ability to populate the rhodamine triplet state (T$_1$) and hence to produce $^1$O$_2$, which is considered to trigger the apoptotic cell death.[21]

Figure 25:
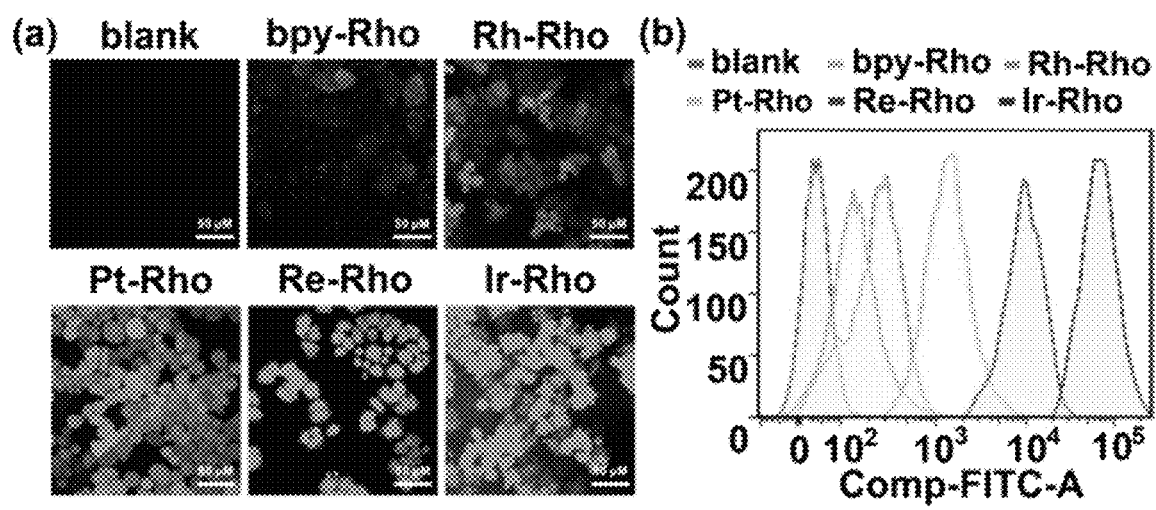
FIG. 25 shows DCFH-DA assay for the evaluation of intracellular ROS production of bpy-Rho and M-Rho (5 µM) in DMEM; incubation with MCF-7 cells in the dark for 30 min followed by 30 min irradiation with 11-W lamp (a) Confocal fluorescence microscopy images and (b) flow cytometry analysis (n=10000 cells) with mean fluorescence intensity per cell.

The intracellular ROS generation ability of bpy-Rho and M-Rho in the human breast carcinoma cells (MCF-7) has also been examined after irradiation with the 11-W lamp for 30 min by using DCFH-DA assay (FIG. 25). The non-fluorescent and cell-permeable H$_2$DCFH-DA dye will be oxidized into strongly fluorescent and cell membrane-impermeable DCF dye by ROS. Both confocal fluorescence microscopic images (FIG. 25a) and flow cytometry analysis (FIG. 25b) indicate that intracellular ROS is significantly generated by the evaluation of DCF fluorescence. In line with the photophysical results, Ir-Rho is found to have the highest ROS generation ability, while the blank and bpy-Rho can only generate negligible or a little amount of ROS under the same condition.

In order to investigate the intracellular localization of bpy-Rho and M-Rho, MCF-7 cells have been co-stained with the mitochondria-specific probe, MitoTracker Green. Confocal microscopy shows that all of them are specifically localized in the mitochondria (FIG. 4), suggesting that the modified rhodamine ligand and metal complexes retain the mitochondria-targeting ability of rhodamine. According to the overlapping of fluorescence signals between the compounds and MitoTracker Green and the Pearson's colocalization coefficients, the metal complexes M-Rho are essentially localized in the mitochondria whereas the ligand bpy-Rho is relatively less mitochondria-localized. It is interesting to note that the incorporation of transition metal systems into the rhodamine-tethered ligand results in stronger mitochondria-targeting properties, probably due to the balanced interplay between the cationic charge and lipophilicity.

Figure 26:
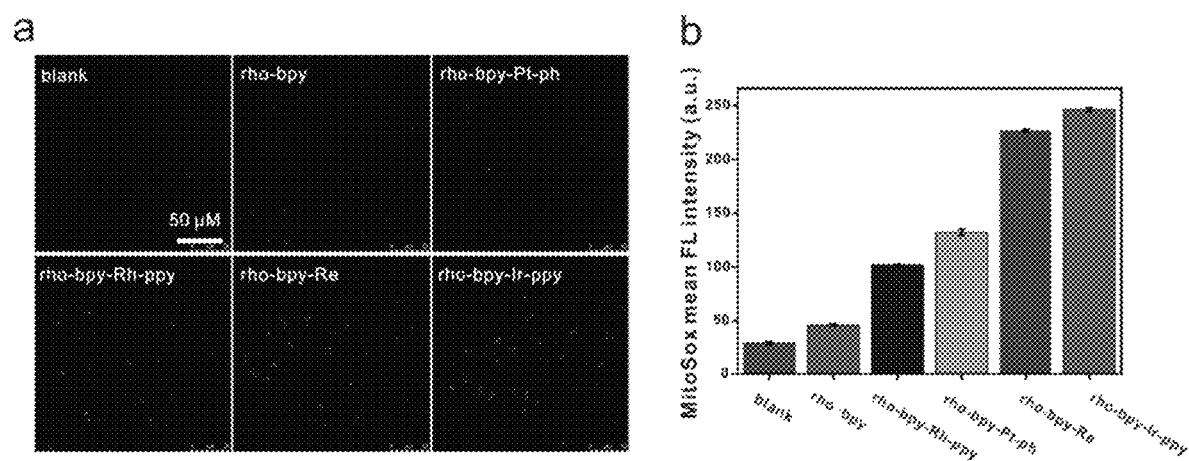
FIG. 26 shows use MitoSox indicator to evaluate the production of ROS in mitochondria after incubation of MCF-7 cells with rhodamine metal complexes. (a) Confocal fluorescence microscopic images of MCF-7 cells treated with MitoSOX (1.0 µM) according to the treatment variables, including with coincubation with bpy-Rho and M-Rho (10 µM), 11 W lamp irradiation for 10 min. (b) Flow cytometry analysis of MCF-7 cells (n=10000 cells) after treatment with MitoSox and different Rhodamine-metal Complexes mean fluorescence intensity per cell.

On the basis of the results of intracellular ROS production and colocalization study, it is reasonable to anticipate that the ROS is essentially generated within the mitochondria. MitoSOX Red reagent, a mitochondrial ROS indicator, is also used to probe specifically the generation of mitochondria-localized ROS. Intense red fluorescence from the oxidation of MitoSOX is observed in both confocal fluorescence microscopy images (FIG. 26a) and flow cytometry analysis (FIG. 26b) of MCG-7 cells incubated with MitoSOX and M-Rho. With same treatment of bpy-Rho or in the untreated control, only very weak red fluorescence has been detected, indicative of remarkable mitochondria-localized ROS generation in M-Rho. In view of all these results, both the mitochondria-targeting and enhanced photosensitizing properties are unique to M-Rho, showing the synergy between the rhodamine unit and transition metal system.

Figure 27:
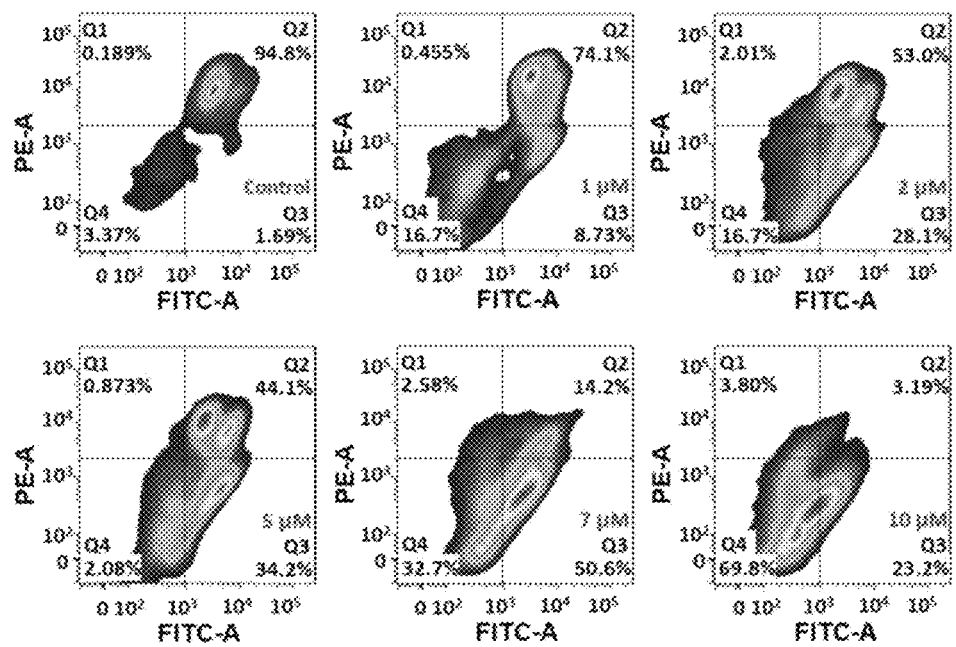
FIG. 27 shows effect of rho-bpy-Ir-ppy Constructs on Mitochondrial Depolarization of Cancer Cells.
Figure 28:
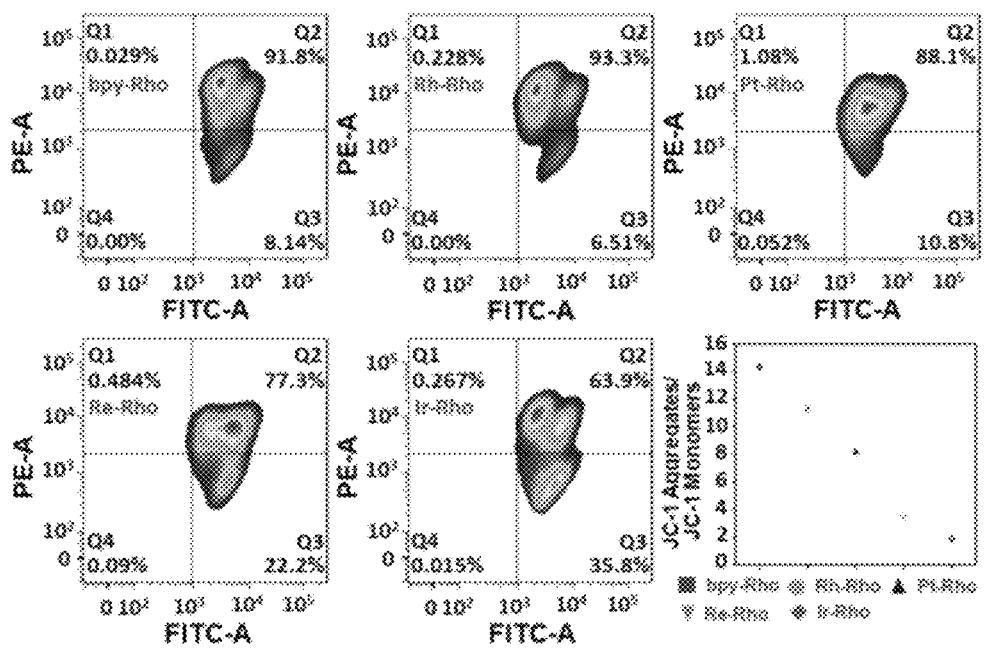
FIG. 28 shows flow-cytometry-based JC-1 assay as a measure of mitochondrial depolarization induced by bpy-Rho and M-Rho.

In order to confirm that the mechanism of cell death is arising from the photo-cytotoxicity of M-Rho, a flow-cytometry-based JC-1 assay was adopted to investigate the change in mitochondrial membrane potential ($\Delta\Psi m$). Mitochondrial depolarization occurs as a result of mitochondrial dysfunction and is commonly regarded as a hallmark of apoptosis.[22] As a lipophilic and cationic dye, JC-1 can selectively translocate into mitochondria. The J-aggregate form of JC-1 with intense red fluorescence is formed in healthy cells with high $\Delta\Psi m$, while green fluorescent monomeric form exists in the apoptotic cells with low $\Delta\Psi m$.[23,24] No obvious change in the $\Delta\Psi m$ of MCF-7 cells is found in the vehicle control, as evident from dominant red J-aggregates (94.8%) with minimal green JC-1 monomers (1.69%) (FIG. 27). In contrast, a dramatic increase in the green fluorescence with a concomitant drop in red fluorescence is observed for the MCF-7 cells treated with increasing concentration of Ir-Rho upon irradiation. This strongly indicated an increase in mitochondrial depolarization and hence apoptosis, which are responsible for the photo-cytotoxicity. Parallel experiments for bpy-Rho and M-Rho at the same concentration suggest that Ir-Rho results in significantly higher mitochondrial dysfunction and eventually increased apoptosis (FIG. 28). On the basis of the decreased ratio of JC-1 aggregates/JC-1 monomers in the cells with $^1O_2$ generated, the lowest ratio of 1.79 for Ir-Rho shows the enhanced effect of PDT on the mitochondrial-regulated apoptosis, relative to the others (bpy-Rho, 14.23; Rh-Rho, 11.28; Pt-Rho, 8.16; Re-Rho, 3.48).

Figure 4:
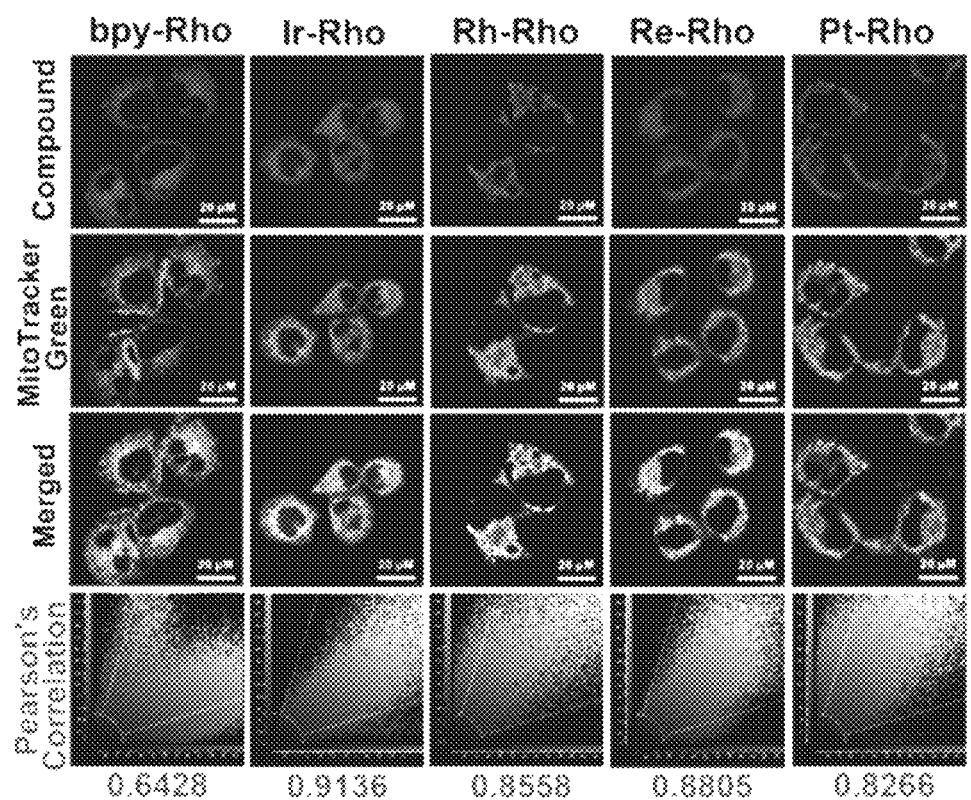
FIG. 4 shows Laser-scanning confocal microscopic images of MCF-7 cells treated with 5 µM bpy-Rho and M-Rho and MitoTracker Green.

We envisioned that the mitochondria-targeting bpy-Rho and M-Rho would exhibit good selectivity towards tumor cells that possess more active mitochondria. Flow cytometry has been used to evaluate the tumor cell selectivity of bpy-Rho and M-Rho by incubation in different cell lines, including tumor cells (MCF-7, human breast cancer cells; A549, human lung cancer cells; 4T1, mouse breast cancer cells) and normal cells (MCF-10A, human breast cells; 293T, human kidney cells; bEnd3, mouse microvascular endothelial cells). The results indicate that Ir-Rho possessed the highest uptake efficiency and affinity to tumor cells (FIG. 4). Based on the previous studies, a contrast index (CI) higher than 2.5 is considered as substantial accumulation in a tumor,[25] and therefore Ir-Rho is found to be selective towards tumor cells from their CI values of greater than 2.5 to 4T1, A549, and MCF-7.

It is known that the selectivity toward tumor cells is not only due to the enhanced mitochondrial membrane potential in typical tumor cells, but also highly dependent on the lipophilic/hydrophilic character of the photosensitizers.[7,26] Octanol-water partition coefficients (log $P_{o/w}$)[27] of bpy-Rho and M-Rho have been measured in order to study their lipophilic/hydrophilic characters. The higher is the log $P_{o/w}$ value associated with the dye, the higher is its lipophilic character. The log $P_{o/m}$ values of bpy-Rho, Ir-Rho, Re-Rho, Pt-Rho and Rh-Rho are determined to be 0.49, −0.39, 0.41, 1.26, and −1.05, respectively. Our results indicate that the more hydrophilic (negative log $P_{o/w}$ values) dyes studied show a high degree of tumor cell selectivity. Previous studies demonstrated that the tumor cell selectivity is more likely to occur when the lipophilic/hydrophilic character of any cationic mitochondrial drug falls within a narrow range of $P_{o/w}$ values close to that of the prototypical mitochondrial dye rhodamine 123 (log $P_{o/w}$=−0.62).[26a] Our data show that the log $P_{o/w}$ value of Ir-Rho is very close and the closest among other compounds to rhodamine 123. The best tumor cell selectivity of Ir-Rho is consistent with this prediction. Other factors, including OTAP1B3 subtype of organic anion transporter peptides (OATPs),[28] affecting the tumor cell selectivity cannot be precluded.

Figure 5:
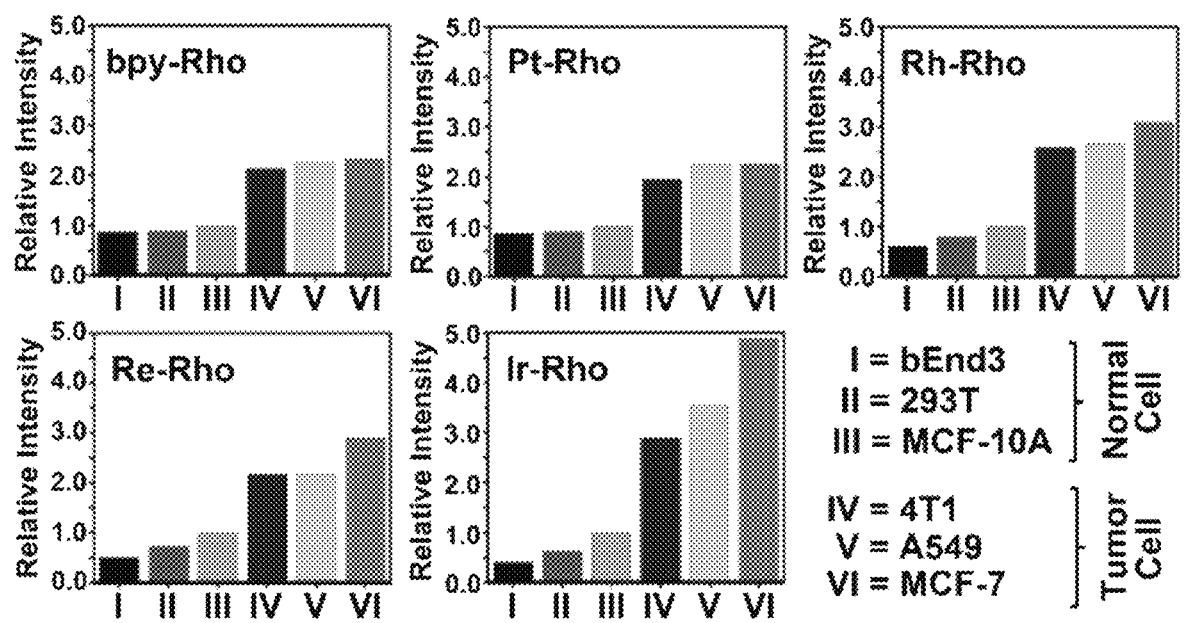
FIG. 5 shows flow cytometry analysis (n=10 000 cells) of bpy-Rho and M-Rho in normal cells (bEnd3, 293T, MCF-10A) and tumor cells (4T1, A549, MCF-7) with normalized fluorescence intensity.
Figure 6:
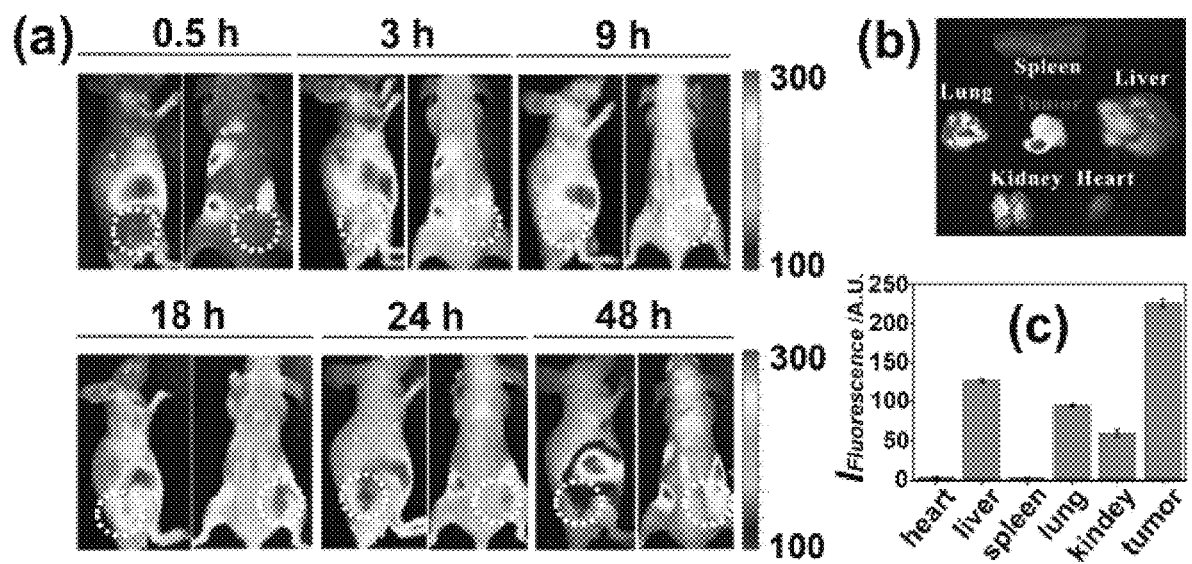
FIG. 6 shows (a) In vivo NIFR images of MCF-7 tumor-bearing nude mice from 0 to 48 h after injection of Ir-Rho (200 µM, 150 µl). (b) Ex vivo NIR images and (c) fluorescence intensity of dissected organs and tumor at 24 h post injection.
Figure 7:
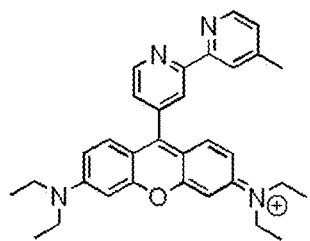
FIG. 7 shows $^1$H (top) and $^{13}$C (bottom) NMR spectra of bpy-Rho in $CD_3CN$ at 298K.
Figure 7:
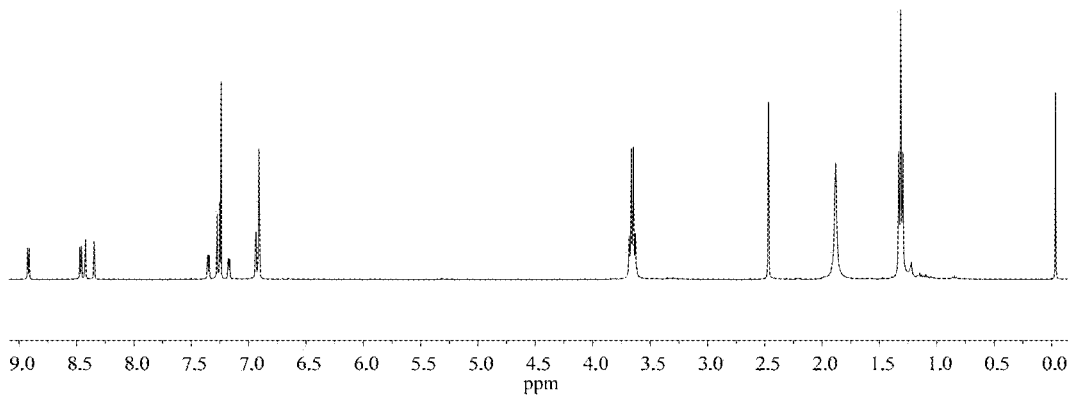
Figure 7:
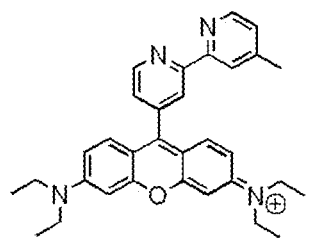
Figure 7:
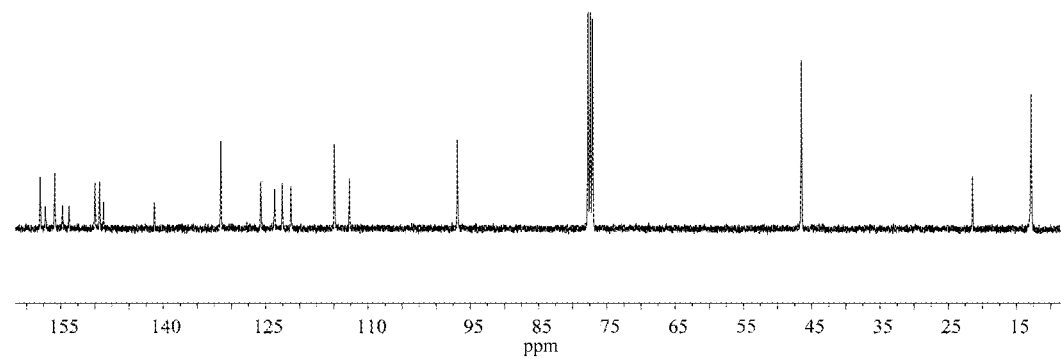
Figure 8:
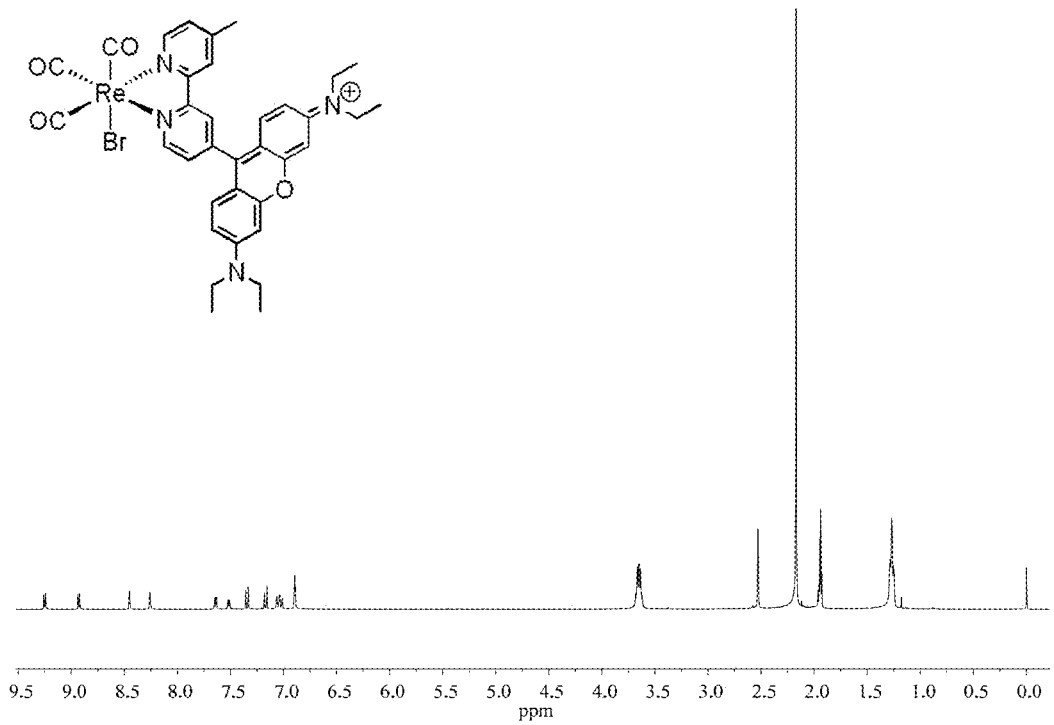
FIG. 8 shows $^1$H (top) and $^{13}$C (bottom) NMR spectra of Re-Rho in CD3CN at 298K.
Figure 8:
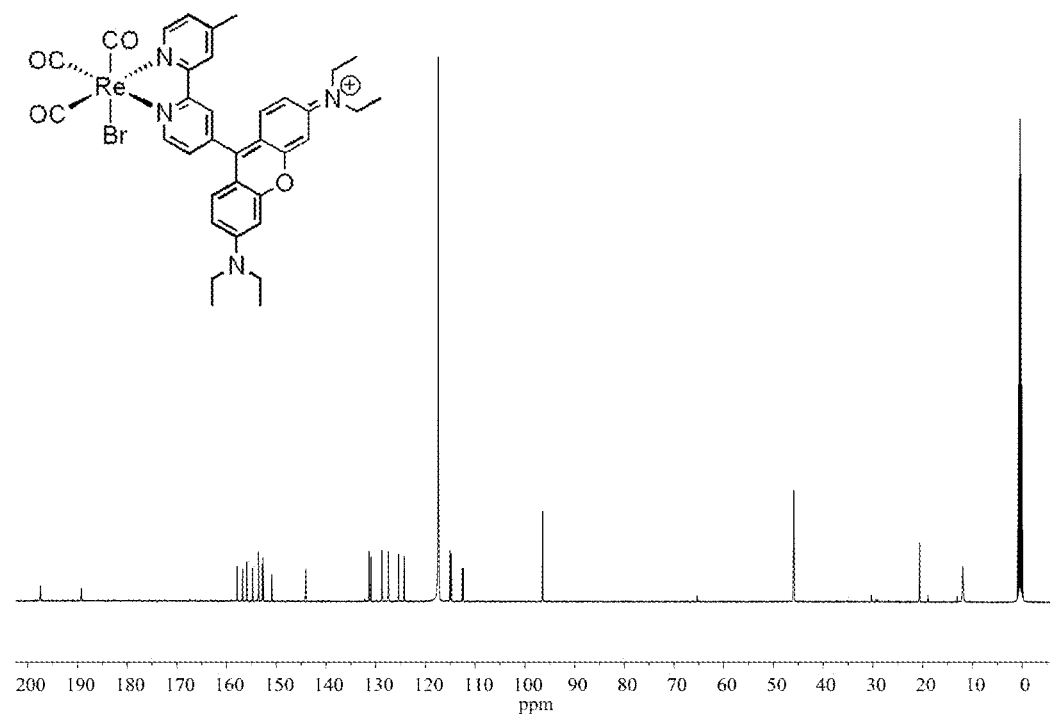
Figure 9:
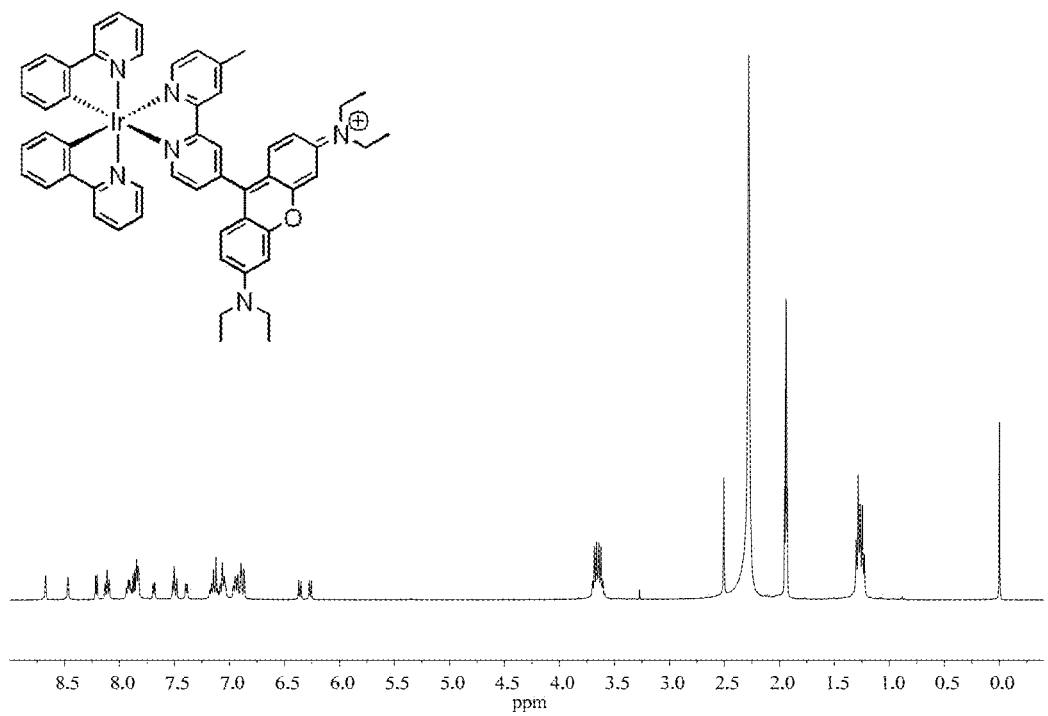
FIG. 9 shows $^1$H (top) and $^{13}$C (bottom) NMR spectra of Ir-Rho in $CD_3CN$ at 298K.
Figure 9:
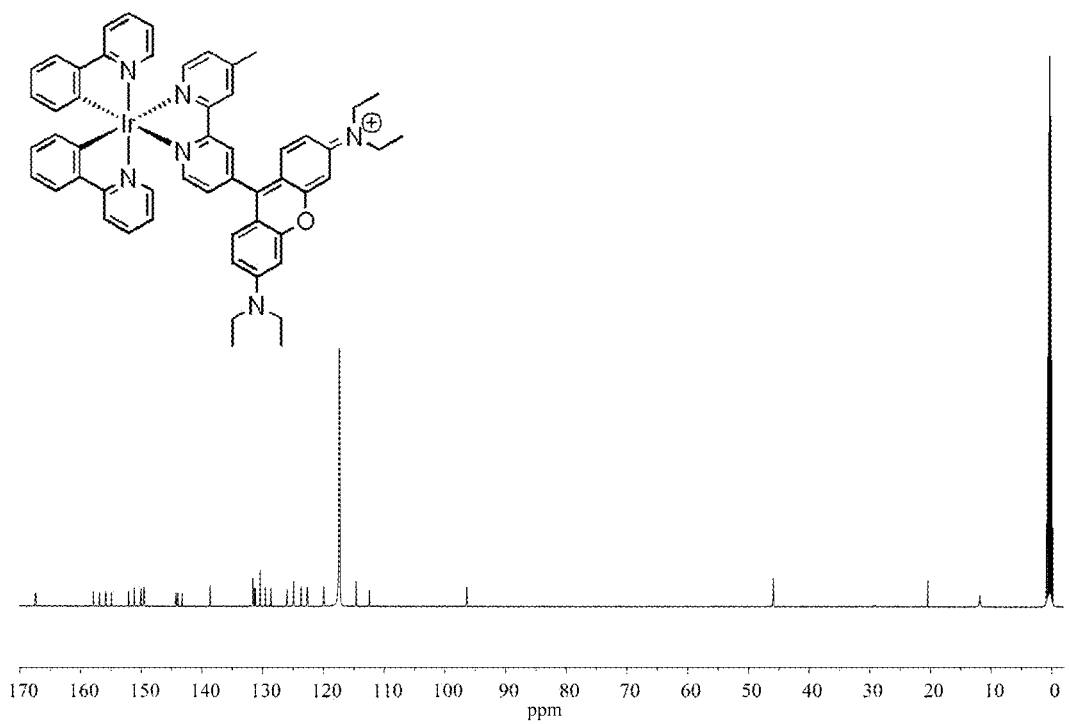
Figure 10:
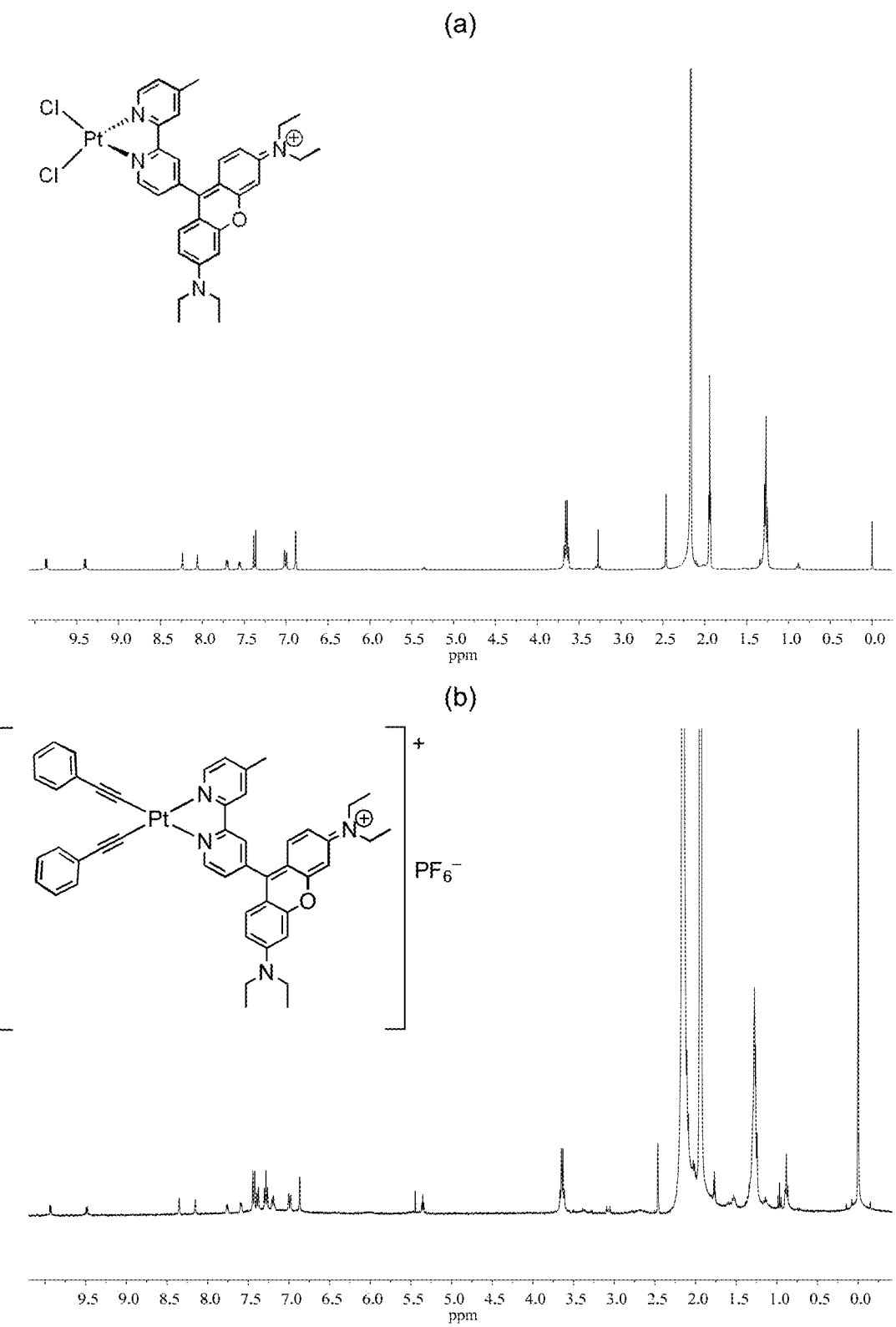
FIG. 10 shows $^1$H NMR spectra of Pt-Cl (top) and Pt-Rho (bottom) in $CD_3CN$ at 298K.
Figure 11:
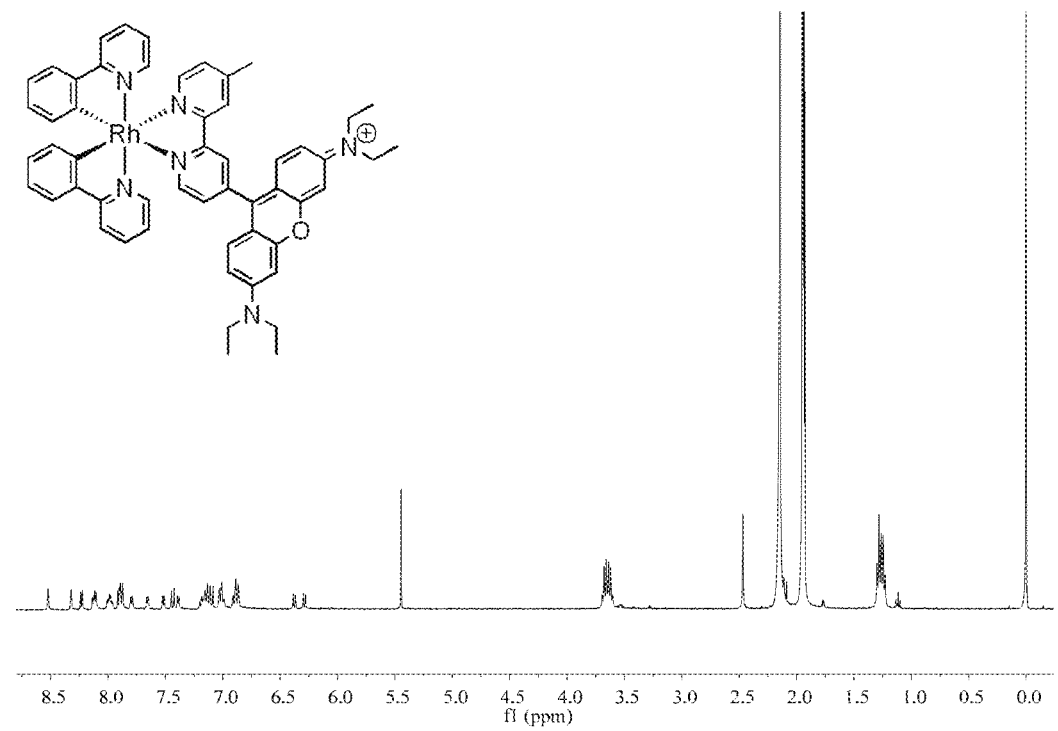
FIG. 11 shows $^1$H NMR spectrum of Rh-Rho in $CD_3CN$ at 298K.
Figure 12:
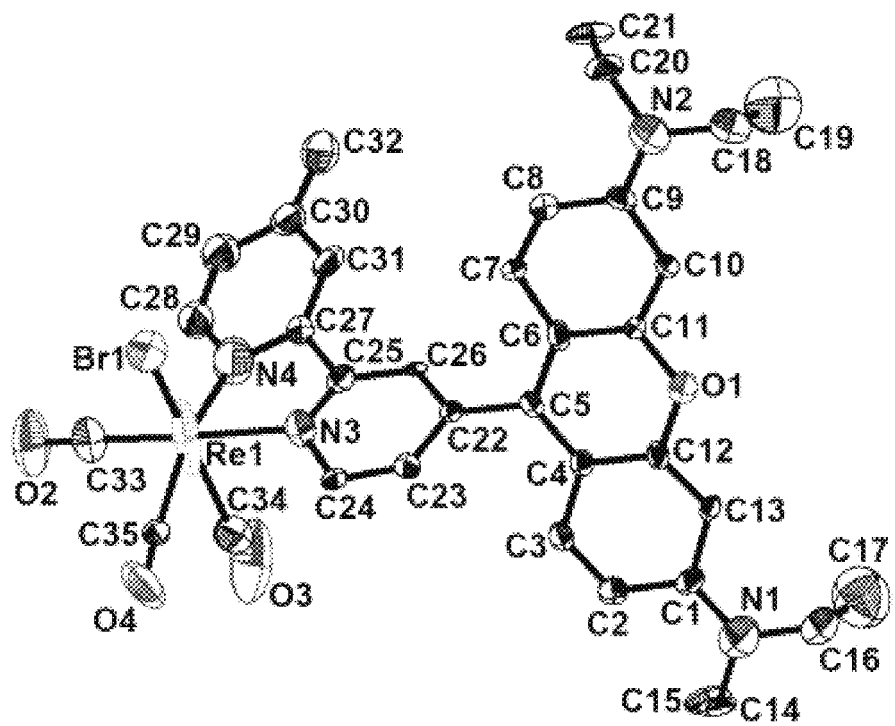
FIG. 12 shows X-ray structure of Re-Rho (thermal ellipsoids are drawn at the 35% probability level, hydrogen atoms and cation are omitted for clarity).
Figure 29:
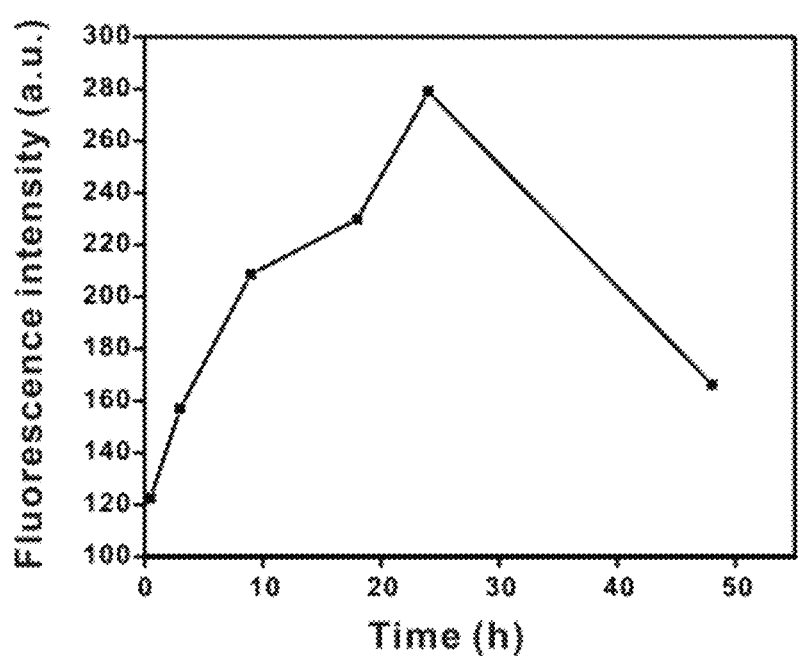
FIG. 29 shows fluorescent intensity of tumor tissue at different time points.

The tumor cell selectivity of Ir-Rho has been further evaluated by in vivo near-infrared fluorescence (NIRF) imaging by monitoring the in vivo biodistribution and tumor accumulation of Ir-Rho. The in vivo NIRF images demonstrate a steady increase of tumor uptake of Ir-Rho, which peaks at 24 h (FIG. 5a and FIG. 29) after intravenous (i.v.) injection into MCF-7 tumor-bearing mice via the tail vein. At 24 h post-injection, tumors and major organs were excised for ex vivo NIRF imaging to determine the tissue distribution of Ir-Rho. As shown in FIG. 5b,c, Ir-Rho exhibits good tumor accumulation and relatively low liver uptake, further indicating its good selectivity towards tumor cells.

In summary, we have established a versatile strategy to combine a rhodamine unit with a variety of transition metal centers to afford mitochondria-targeting photosensitizers. Facile generation of rhodamine triplet excited states, which are involved in $^1O_2$ formation, can be achieved. M-Rho, receiving the synergistic effects of large molar extinction coefficients in the visible region, low dark cytotoxicity, high photostability as well as selective tumor cell uptake, has been demonstrated as a promising candidate in PDT application. This work opens up a new avenue for the exploitation of the rhodamine system through the efficient population of triplet state and provides a new direction in the development of promising photosensitizers. Modification of such hybrid systems with other organic chromophores, such as fluorescein, Si-rhodamine and Si-fluorescein, as well as the exploration of other applications in photocatalytic reactions, DSSC and solar cells are underway.

EXAMPLES

Materials and Reagents

All the solvents for synthesis were all of analytical grade. Iridium(III) chloride hydrate, and 4,4'-dimethyl-2,2'-bipyridine were purchased from Aldrich Chemical Company. $Re_2(CO)_{10}$ was purchased from Stream. Rhodium(III) chloride hydrate was purchased from Innochem. $Re(CO)_5Br$ was obtained by dropwise addition of $Br_2$ into the DCM solution of $Re_2(CO)_{10}$ until the solution becomes light yellow and then evaporated to dryness, which was used without further purification. 4'-methyl-[2,2'-bipyridine]-4-carbaldehyde,[1] [$Ir_2(ppy)_4$-$Cl_2$],[2] cis-[$(DMSO)_2PtCl_2$],[3] and [$Rh_2(ppy)_4$-$Cl_2$],[4] $Re(bpy)(CO)_3$,[5] $Ir(ppy)(bpy)$[6] were synthesized according to the literature methods.

Physical Measurements and Instrumentation

The UV-vis absorption spectra were taken on Cary 60 UV-vis spectrophotometer. Steady-state emission spectra at room temperature were recorded on an Edinburgh Instruments FLS980 fluorescence spectrometer. Quartz cuvettes (path length=1 cm) were used in all spectrophotometric and fluorometric measurements. NMR spectra were recorded on a Bruker AVANCE 400 ($^1$H NMR for 400 MHz and $^{13}$C NMR for 100 MHz) Fourier transform NMR spectrometer with chemical shifts reported relative to tetramethylsilane, $(CH_3)_4Si$. High-resolution MS spectra were performed on an Orbitrap Fusion Tribrid mass spectrometer. Elemental analyses of the newly synthesized complexes were preformed on a Elementar Vario EL Cube elemental analyzer at Sun Yat-sen University. The nanosecond time-resolved transient-difference absorption spectra were detected by using Edinburgh LP920 instruments (Edinburgh Instruments, U.K.). All solutions for transient absorption studies were degassed on a high-vacuum line in a two-compartment cell consisting of a 10-ml Pyrex bulb and a 1-cm or 4-mm path length quartz cuvette and sealed from the atmosphere by a Bibby Rotaflo HP6 Teflon stopper. The solutions were rigorously degassed with at least four successive freeze-pump-thaw cycles. Emission lifetime measurements were performed using a conventional laser system. The excitation source used was a 355-nm output (third harmonic) of a Spectra-Physics Quanta-Ray Q-switched GCR-150-10 pulsed Nd-YAG laser. Luminescence decay signals were detected by a Hamamatsu R928 PMT and recorded on a Tektronix Model TDS-620A (500 MHz, 2 GS/s) digital oscilloscope and analyzed using a program for exponential fits. Absolute quantum yields were measured by HAMAMATSU-C11347.

X-ray Crystal Structure Determination

Single crystals of Re-bpy suitable for X-ray diffraction studies were grown by slow vapour diffusion of diethyl ether into actonitrile solution of Re-bpy. Single-crystal X-ray diffraction analysis of Re-bpy was performed on a Bruker APEX-II CCD diffractometer with graphite-monochromated Mo-Kα radiation (λ=0.71073 Å) at 150K. Empirical absorption correction using spherical harmonics, implemented in SCALE3 ABSPACK scaling algorithm. The structure was solved and refined by the SHELXL-2004/7 program package.[7] CCDC-1838920 contains the supplementary crystallographic data for this paper. These data can be obtained free of charge from The Cambridge Crystallographic Data Centre via www.ccdc.cam.ac.uk/data_request/cif.

Singlet oxygen emission was detected by using FLS-980 spectrofluorometer. All of the compounds were dissolved in $CH_3CN$. The absorbance at 532 nm was adjusted to be around 1.7 for all the compounds. Upon measurements, an 850 nm long-pass filter was inserted in between the sample and the detector to avoid many high-order diffraction from the visible emission.

Singlet oxygen quantum yield was determined by comparing the $^1O_2$ emission intensity of Rose Bengal and M-Rho.

Photostability test was performed by using 532 nm laser with 336 mW/cm$^2$ output power as the irradiation source. The compounds were dissolved in $CH_3CN$, and their absorbance were checked after 0, 1, 3, 5, 7, 10 min respectively. Their absorbance at 532 nm was adjusted to be the same initially.

Computational Details

Full geometry optimizations of Re-Rho have been calculated using Gaussian 09W software packages[7] with B3PW91 hybrid functional of DFT without any constrained symmetry in vacuo. The optimized process calculations are performed at the B3PW91/6-31++g* level of theory. Meanwhile, LanL2DZ with effective core potential for Re were used. The lowest triplet (T1) structure was optimized at B3PW91/6-31++g* level of theory. After the geometry optimization, the excitation energies were calculated using the TD-B3PW91/6-31++g*method.

Subcellular Localization

MCF-7 cells (5000 cells) were cultured in eight-well chambered coverglasses (lab-Tek, Nunc, USA) for 24 h. Later, added to the cells to give final complexes concentrations (5 μM). After incubation for 30 min, The cells were treated with Mito-Tracker for 10 min to stain specifically the mitochondria (1:5000 dilution in PBS). After washing three times with PBS, followed by confocal microscopy imaging.

Selective Uptake

Tumor cells (MCF-7/A 549/HepG2/4T1) and normal cells (MCF-10A/293T/L02/NIH-3T3) (1×10$^4$ cells) was cultured in six-well plate for 12 h. and then Cells were changed with a medium containing 5 μM complexes (rho-bpy, rho-bpy-Pt-ph, rho-bpy-Rh-ppy, rho-bpy-Re and rho-bpy-Ir-ppy). Cells were washed three times with PBS after 2 h of incubation, Then the cells were harvested, and the fluorescence intensity of complexes were recorded by flow cytometer.

Intracellular ROS

The MCF-7 cells were seeded in eight-well chambered coverglasses (lab-Tek, Nunc, USA) and six-well plate, incubated for 24 h in 5% $CO_2$ at 37° C. Next, added to compounds (bpy-Rho and M-Rho) in medium make the final concentrations of 5 μM compounds. After irradiation treatment (11 W lamp 30 min), cells were promptly washed with PBS and incubated with 4 μg/ml 2'7'-dichloro-fluoreseindiacetate (DCFH-DA) for 30 min, and intracellular ROS generation was evaluated by flow cytometry and confocal microscopy.

Cell Culture

MCF-7 human breast cancer cells, A549 human lung cancer cells, HepG2 hepatocellular carcinoma cells, 293T human kidney cells and 4T1 mouse breast cancer cells were cultured in DMEM medium (Gibco) supplemented with 10% fetal bovine serum(FBS) (Gibco), 1% penicillin and 1% streptomycin. Cells were incubated at 37° C. in a humidified incubator with 5% $CO_2$. MCF-10A human breast cells, L02 human liver cells and NIH-3T3 mouse embryonic fibroblasts were maintained in an RMPI-1640 medium supplemented with 10% fetal bovine serum (FBS) and 1% penicillin and streptomycin. Cells were incubated at 37° C. in a humidified incubator with 5% $CO_2$.

Measurement of Mitochondrial Membrane Potential

Mitochondrial depolarization was assessed by flow cytometry after incubation with JC-1 Molecular Probes (Thermo Fisher Scientific, USA). Briefly, The MCF-7 cells were seeded in six-well plate, incubated for 24 h in 5% $CO_2$ at 37° C. Next, added to compounds (bpy-Rho and M-Rho) in medium make the final concentrations of 5 uM compounds. After irradiation treatment (11 W lamp 30 min). The cells were resuspended in warm PBS, and incubated with JC-1 (4 µg/ml) for 30 min at 37° C. and 5% $CO_2$. Thereafter the cells were centrifuged, resuspended in 600 µL of PBS, and analyzed immediately on a flow cytometer (Becton Dickinson, San Jose, Calif., USA). Untreated cells were used as negative controls.

Dark Toxicity

The cells were treated and cell viability was determined as described in the experimental section for phototoxicity without irradiation from 1 µM to 10 µM concentration.

Phototoxicity

1. MCF-7 cells were seeded at $8 \times 10^3$-$1 \times 10^4$ cells/well in 96 well plates then incubated for 24 h in 5% $CO_2$ at 37° C. The stock solutions of the complexes(10 mM in DMSO) were diluted to appropriate concentrations with the complete medium and added to the cells to give final complexes concentrations (1, 2, 5, 10 µM). After incubation for 2 h, the well plate were irradiated with 11 W lamp 30 min. To achieve more uniform irradiation, the entire well plate was gently orbited on the shaker. After the irradiation, the cells were again incubated for 2 h, after which the cytotoxicity was determined by CCK8 assay and expressed as a percent of the controls (cells exposed to light in the absence of the complexes).

2. The MCF-7 cells(500 cells/well) were seeded in eight-well chambered coverglasses (lab-Tek, Nunc, USA), and then incubated for 24 h in 5% $CO_2$ at 37° C. Next, added to complexes(rho-bpy, rho-bpy-Pt-ph, rho-bpy-Rh-ppy, rho-bpy-Re and rho-bpy-Ir-ppy) in medium make the final concentrations of 5 µM complexes. After incubation for 2 h, the eight-well plate were irradiated with 11 W lamp 30 min. The flowing, fixed with 4% paraformaldehyde solution. After staining with calcein-AM and (Propidium iodide) PI, Leica TCS SP5 confocal laser scanning microscope (GER) was used to observe the viable and dead cells.

Animals and Tumor Model

Animals received care in accordance with the Guidance Suggestions for the Care and Use of Laboratory Animals. The procedures were approved by the Animal Care and Use Committee (Shenzhen Institutes of Advanced Technology, Chinese Academy of Sciences). Four-8-week-old female BALB/c mice or nude mice (Vital River Laboratory Animal Technology Co. Ltd., China) were subcutaneously injected with MCF-7 cells ($1 \times 10^6$) in the flank region.

Vivo Imaging

The Maestro GNIR Flex imaging system and analysis with software from CRi was used to image tumor-bearing animals over time following i.v. treatment with Ir-Rho (200 µM, 150 µl). At each time point, the mouse was imaged at 600 nm excitation and 650 nm emission. At 24 h post injection, tumors and major organs were excised for ex vivo NIRF imaging to determine the tissue distribution of Ir-Rho. All main organs were cut with similar thickness and imaged at 600 nm excitation and 650 nm emission. The average fluorescence intensity of organs was from a region of interest (ROI) placed over the area of the organs on the image.

Synthesis

The complexes of the invention are synthetized as following Scheme 1:

Scheme 1

Synthesis of rhodamine-metal complexes.[1] (i) $SeO_2$, 1,4-dioxane, reflux; (ii) 3-(diethylamino)phenol, $CH_3COOH$, p-TsOH, chloranil; (iii) $Re(CO)_5Br$, toluene, reflux; (iv) [{Ir(ppy)$_2$Cl}$_2$],[2] MeOH/DCM, reflux; (v) cis-[(DMSO)$_2$PtCl$_2$],[3] toluene, 80° C.; (vi) CuI, phenylacetylene, DMF, diethylamine; (vii) [{Rh(ppy)$_2$Cl}$_2$],[4] MeOH/DCM, reflux. The model complex Re(bpy)(CO)$_3$ and Ir(ppy)$_2$(bpy) are shown for comparison.

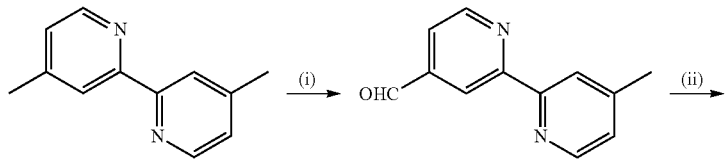

-continued
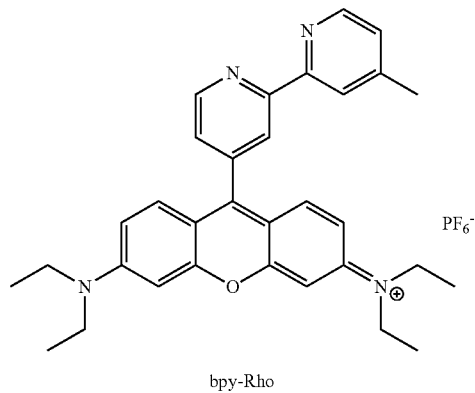
bpy-Rho
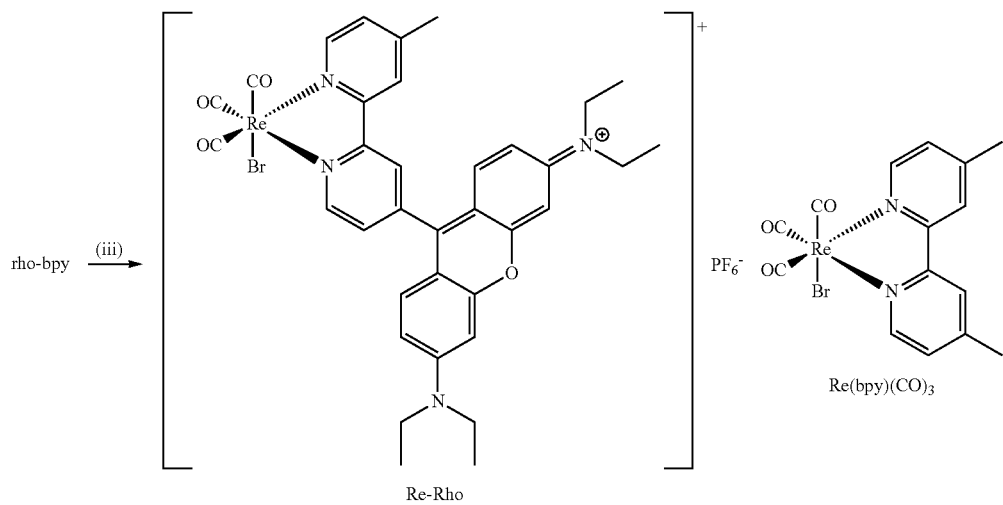
Re-Rho
Re(bpy)(CO)₃
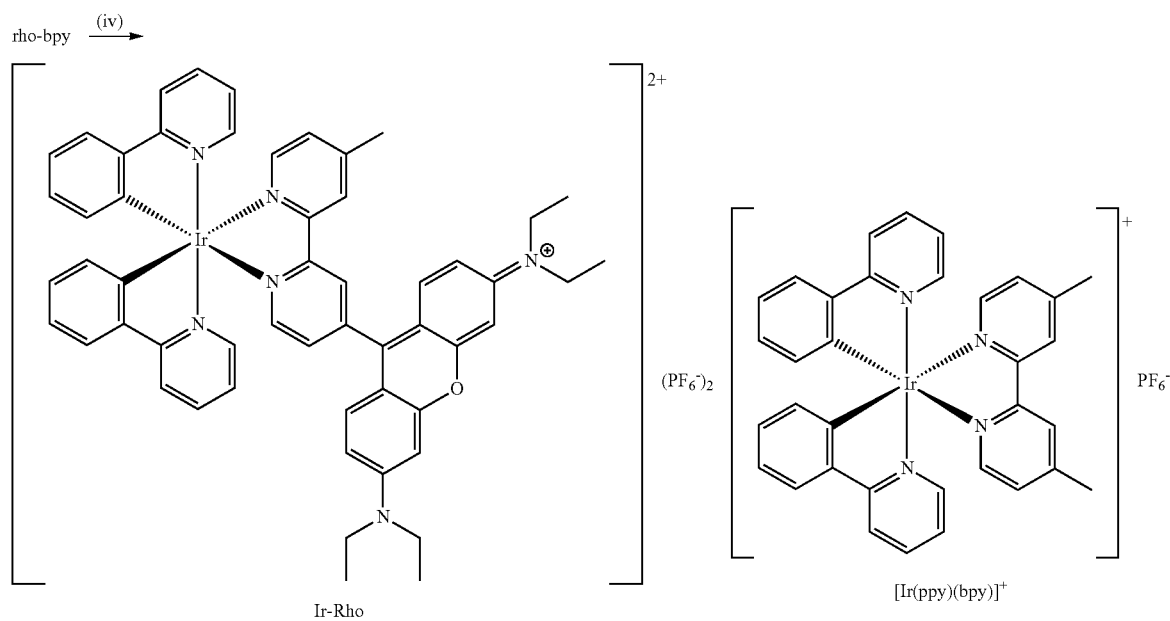
Ir-Rho
[Ir(ppy)(bpy)]⁺

-continued
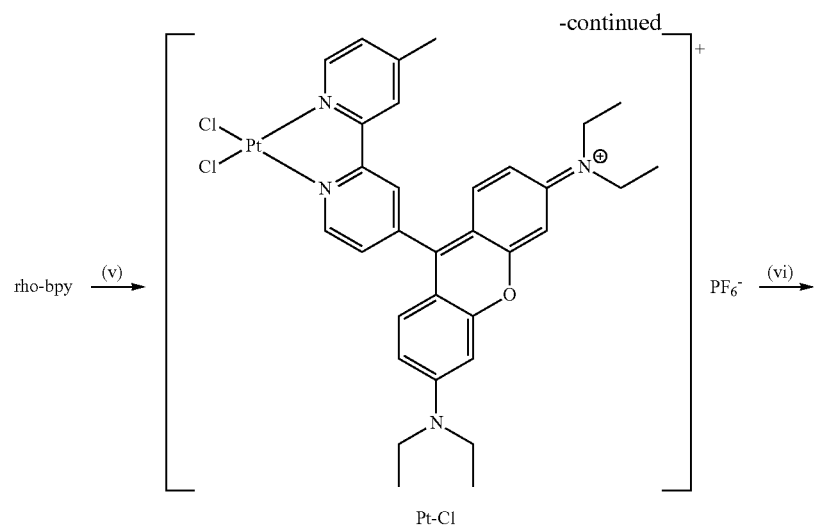
Pt-Cl
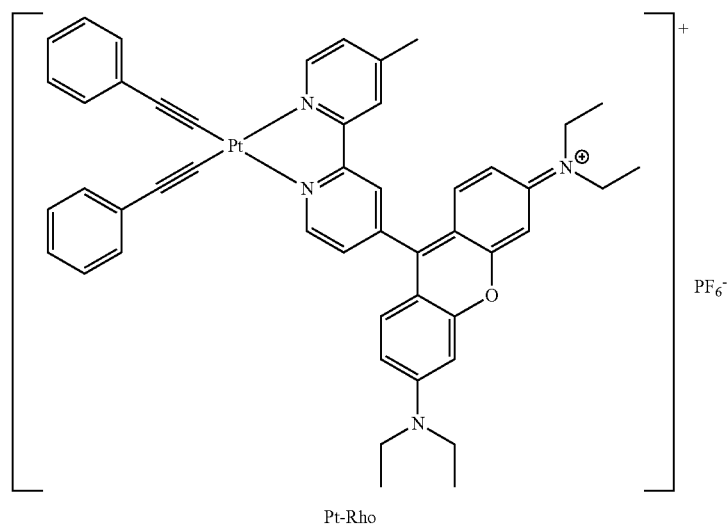
Pt-Rho
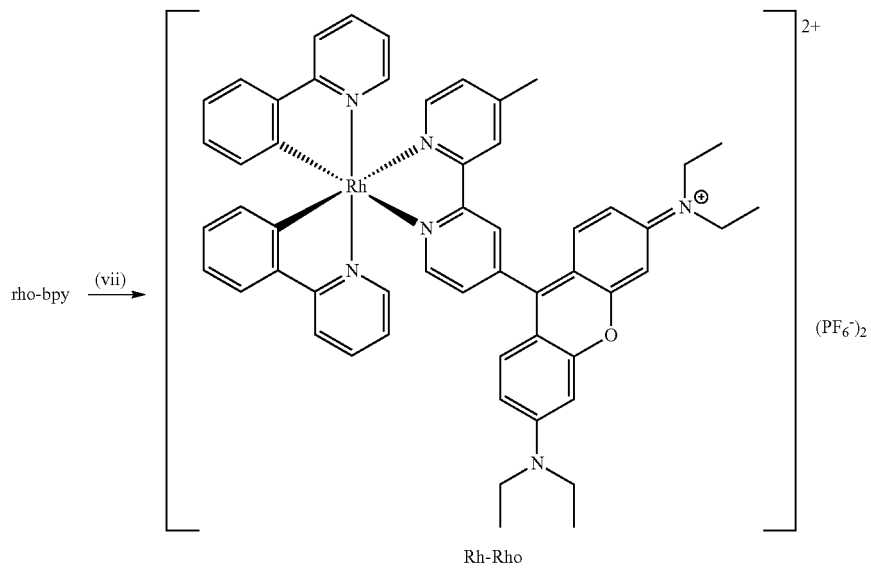
Rh-Rho

N-(6-(diethylamino)-9-(4'-methyl-[2,2'-bipyridin]-4-yl)-3H-xanthen-3-ylidene)-N-ethylethanaminium (bpy-Rho)

A mixture of 4'-methyl-[2,2'-bipyridine]-4-carbaldehyde[1] (1 g, 5 mmol), 3-(diethylamino)phenol (1.7 g, 10 mmol), p-TsOH (0.129 g, 0.75 mmol) and acetic acid (50 mL) was heated to 70° C. and stirred for 7 h. The reaction mixture was cooled to r.t., and the pH was adjusted to above 7 with a 10% NaOH solution. The precipitate was filtered and washed with water (50 mL). The solid was dissolved in $CH_2Cl_2$ (50 mL), to which chloranil (0.615 g, 2.5 mmol) was added. The mixture was stirred for 2 h, and then evaporated to dryness. The residue was purified by column chromatography (silica gel; $CH_2Cl_2/CH_3OH$, 10:1, v/v) to give a purple solid; yield 0.859 g (27%). $^1H$ NMR (400 MHz, $CDCl_3$) δ (ppm): 8.92 (d, J=4.8, 1H), 8.46 (d, J=4.9, 1H), 8.42 (s, 1H), 8.35 (s, 1H), 7.35 (dd, J=4.9, 1.6, 1H), 7.27 (s, 1H), 7.25 (s, 1H), 7.17 (d, J=4.2, 1H), 6.92 (dd, J=12.3, 2.4, 4H), 3.72-3.59 (m, 8H), 2.47 (s, 3H), 1.31 (t, J=7.1, 12H). $^{13}C$ NMR (101 MHz, $CDCl_3$) δ (ppm): 158.01, 157.26, 155.89, 154.74, 153.77, 150.00, 149.31, 148.73, 141.29, 131.57, 125.70, 123.68, 122.58, 121.29, 114.92, 112.74, 96.90, 46.53, 21.45, 12.88. HRMS (ESI). Calcd for $C_{32}H_{35}N_4O$ ([M+H]$^+$): m/z 491.2805. Found: m/z 491.2794.

Re-Rho bpy-Rho (100 mg, 0.16 mmol) and $Re(CO)_5Br$ (65 mg, 0.16 mmol) were refluxed in toluene overnight in the dark under nitrogen. The solution was cooled to room temperature, and then evaporated to dryness. The crude was purified by neutral $Al_2O_3$ column chromatography ($CH_2Cl_2/CH_3CN$). Subsequent recrystallization of the complex by diffusion of diethyl ether vapor into a solution of the complex in acetonitrile. Yield: 126 mg (80%). $^1H$ NMR (400 MHz, $CD_3CN$) δ (ppm): 9.25 (d, J=5.7, 1H), 8.93 (d, J=5.7, 1H), 8.45 (d, J=1.0, 1H), 8.26 (s, 1H), 7.64 (dd, J=5.6, 1.7, 1H), 7.52 (d, J=4.9, 1H), 7.34 (d, J=9.6, 1H), 7.16 (s, 1H), 7.08-6.99 (m, 2H), 6.90 (d, J=2.0, 2H), 3.65 (dd, J=7.1, 4.3, 8H), 2.53 (s, 3H), 1.35-1.21 (m, 12H). $^{13}C$ NMR (126 MHz, $CD_3CN$) δ (ppm): 197.45, 189.22, 157.87, 156.75, 155.96, 154.75, 153.58, 152.80, 152.65, 150.87, 144.02, 131.32, 130.95, 128.75, 127.45, 125.41, 124.26, 114.94, 112.50, 96.42, 45.92, 20.60, 11.91. HRMS (ESI). Calcd for $C_{35}H_{35}BrN_4O_4Re$ ([M+H]$^+$): m/z 841.1394. Found: m/z 841.1385. Elemental analysis (%) calcd for $C_{35}H_{35}BrF_6N_4O_4PRe \cdot CH_3OH \cdot 3CH_3COCH_3$(found): C 45.30 (45.65), H 4.82 (4.66), N 4.70 (4.98).

Ir-Rho

A mixture of [{Ir(ppy)$_2$Cl}$_2$][2] (86 mg, 0.08 mmol) and bpy-Rho (100 mg, 0.16 mmol) in 20 mL of methanol/dichloromethane (1:1 v/v) was refluxed under an inert atmosphere of nitrogen in the dark for 12 h. The solution was then cooled to room temperature, and $KPF_6$ (30 mg, 0.16 mmol) was added to the solution. The mixture was stirred for 30 min at room temperature and then evaporated to dryness. The residue was purified by column chromatography (silica gel; $CH_2Cl_2/CH_3OH$). Yield 152 mg (74%). $^1H$ NMR (400 MHz, $CD_3CN$) δ (ppm): 8.67 (s, 1H), 8.47 (s, 1H), 8.21 (d, J=5.6, 1H), 8.11 (t, J=7.4, 2H), 7.88 (dd, J=18.4, 12.4, 6.8, 6H), 7.69 (d, J=5.7, 1H), 7.50 (t, J=7.2, 2H), 7.39 (d, J=5.5, 1H), 7.11 (ddd, J=24.2, 14.0, 6.7, 1H), 7.00-6.81 (m, 5H), 6.36 (d, J=7.4, 1H), 6.26 (d, J=7.5, 1H), 3.65 (dq, J=14.3, 7.0, 8H), 2.51 (s, 3H), 1.37-1.18 (m, 12H). $^{13}C$ NMR (126 MHz, $CD_3CN$) δ (ppm): 167.43, 157.87, 156.91, 155.88, 154.91, 152.11, 151.20, 150.12, 150.06, 149.55, 144.29, 144.03, 143.28, 138.67, 131.63, 131.39, 131.19, 130.43, 129.58, 128.63, 126.00, 124.91, 123.65, 122.67, 119.94, 114.62, 112.46, 96.40, 45.84, 20.43, 11.87. HRMS (ESI). Calcd for $C_{54}H_{51}ON_6F_6IrP$ ([M+H]$^+$): m/z 1137.3390. Found: m/z 1137.3392. Elemental analysis (%) calcd for $C_{54}H_{51}ON_6F_{12}IrP_2 \cdot 2CH_3OH \cdot 2CH_3COCH_3$ (found): C 50.92 (50.66), H 4.89 (4.66), N 5.75 (5.44).

Pt—Cl bpy-Rho (100 mg, 0.16 mmol), [3]cis-[(DMSO)$_2$PtCl$_2$] (68 mg, 0.16 mmol), and $CH_2Cl_2$ (20 mL) were stirred at r.t. overnight under an atmosphere of nitrogen, during which time a deep purple precipitate appeared. The product was collected by filtration and washed with diethyl ether (2×3 mL), which was used in next step without further purification. Yield: 108 mg (75%). $^1H$ NMR (400 MHz, $CD_3CN$) δ (ppm): 9.87 (d, J=6.0, 1H), 9.40 (d, J=6.1, 1H), 8.24 (d, J=1.5, 1H), 8.06 (s, 1H), 7.70 (dd, J=6.0, 1.8, 1H), 7.55 (d, J=6.0, 1H), 7.37 (d, J=9.6, 2H), 7.01 (dd, J=9.6, 2.5, 2H), 6.88 (d, J=2.4, 2H), 3.65 (q, J=7.2, 8H), 2.46 (s, 3H), 1.27 (t, J=7.0, 12H).

Pt-Rho

A 100 mg (0.11 mmol) sample of Pt—Cl, 5 mg of CuI, 0.1 ml (1.0 mmol) of phenylacetylene, 2 ml of DMF, and 1.5 ml of diethylamine were sonicated for 4 h. The flask was chilled, and the precipitate was collected by filtration and washed with ether. Yield: 77 mg (68%). $^1H$ NMR (400 MHz, $CD_3CN$) δ (ppm): 9.93 (d, J=5.5, 1H), 9.48 (d, J=6.0, 1H), 8.35 (s, 1H), 8.15 (s, 1H), 7.75 (s, 1H), 7.60 (s, 2H), 7.43 (d, J=9.1, 3H), 7.39 (d, J=7.0, 2H), 7.32-7.25 (m, 3H), 7.20 (d, J=8.6, 3H), 6.99 (d, J=9.6, 2H), 6.87 (d, J=2.4, 2H), 3.64 (dd, J=14.3, 7.1, 8H), 2.46 (s, 3H), 1.38-1.21 (m, 12H).

Rh-Rho

The synthetic procedure was similar to that of complex Ir-Rho except that [{Rh(ppy)$_2$Cl}$_2$] was used instead of [{Ir(ppy)$_2$Cl}$_2$]. Yield: 70%. $^1H$ NMR (400 MHz, $CD_3CN$) δ (ppm): 8.52 (s, 1H), 8.32 (s, 1H), 8.23 (d, J=5.4, 1H), 8.12 (dd, J=7.9, 4.7, 2H), 8.02-7.95 (m, 2H), 7.89 (dd, J=9.8, 6.7, 3H), 7.80 (d, J=5.2, 1H), 7.66 (d, J=5.3, 1H), 7.52 (d, J=5.4, 1H), 7.44 (d, J=9.6, 1H), 7.39 (d, J=5.3, 1H), 7.21-7.08 (m, 5H), 7.04-6.98 (m, 3H), 6.92-6.86 (m, 3H), 6.38 (d, J=7.7, 1H), 6.29 (d, J=7.7, 1H), 3.65 (dq, J=14.5, 7.1, 8H), 2.47 (s, 3H), 1.26 (dt, J=14.3, 7.1, 12H).

REFERENCES

[1] D. E. J. G. J. Dolmans, D. Fukumura, R. K. Jain, *Nature Reviews Cancer* 2003, 3, 380-387.

[2] S. S. Lucky, K. C. Soo, Yong Zhang, *Chem. Rev.* 2015, 115, 1990-2042.

[3] I. B. N. L. Oleinick, R. L. Morris, I. Belichenko *Photochem. Photobiol. Sci.* 2002, 1, 1-21.

[4] X. Chen, T. Pradhan, F. Wang, J. S. Kim, Juyoung Yoon, *Chem. Rev.* 2012, 112, 1910-1956.

[5] L. G. Lee, S. L. Spurgeon, C. R. Heiner, S. C. Benson, B. B. Rosenblum, S. M. Menchen, A. Constantinescu, K. G. Upadhya, J. M. Cassel, *Nucleic Acids Research* 1997, 25, 2816-2822.

[6] J. R. Lakowicz, *Principles of Fluorescence Spectroscopy*, 3rd ed.; Springer: New York, 2006; pp 67-69.

[7] Silvia H. D. Lacerda, A. Abraham, T. C. Stringfellow, G. L. Indig, *Photochem. Photobiol.* 2005, 81, 1430-1438.

[8] B. Calitree, D. J. Donnelly, J. J. Holt, M. K. Gannon, C. L. Nygren, D. K. Sukumaran, J. Autschbach, M. R. Detty, *Organometallics* 2007, 26, 6248-6257.

[9] S. Davis, M. J. Weiss, J. R. Wong, T. J. Lampidis, L. B. Chen, *J. Biol. Chem.* 1985, 260, 13844-13850.

[10] J. Moan, K. Berg, *Photochem. Photobiol.* 1991, 53, 549-553.

[11]a) A. Sasnauskien, J. Kadziauskas, N. Vezelyte, V. Jonusiene, V. Kirveliene, *Apoptosis* 2009, 14, 276-286; b) D. Kessel, Y. Luo, *Cell Death and Differentiation* 1999, 6, 28-35; c) T. J. Dougherty, C. J. Gomer, B. W. Henderson, G. Jori, D. Kessel, M. Korbelik, J. Moan, Q. Peng, *J. Natl. Cancer Inst.* 1998, 90, 889-905.

[12]a) J. E. Hill, M. K. Linder, K. S. Davies, G. A. Sawada, J. Morgan, T. Y. Ohulchanskyy, M. R. Detty, *J. Med. Chem.* 2014, 57, 8622-8634; b) M. R. Detty, P. N. Prasad, D. J. Donnelly, T. Ohulchanskyy, S. L. Gibson, R. Hilf, *Bioorg. Med. Chem.* 2004, 12, 2537-2544; d) K. A. Leonard, J. P. Hall, M. I. Nelen, S. R. Davies, S. O. Gollnick, S. Camacho, A. R. Oseroff, S. L. Gibson, R. Hilf, M. R. Detty, *J. Med. Chem.* 2000, 43, 4488-4498.

[13]a) V. W. W. Yam, K. M. C. Wong, *Chem. Commun.* 2011, 11579-11592; b) K. K.-W. Lo, *Acc. Chem. Res.* 2015, 48, 2985-2995; c) J. Lee, H.-F. Chen, T. Batagoda, C. Coburn, P. I. Djurovich, M. E. Thompson, S. R. Forrest, *Nature Materials,* 2015, 15, 92-98; d) M. T. Whited, P. I. Djurovich, S. T. Roberts, A. Durrell, C. W. Schlenker, S. E. Bradforth, M. E. Thompson, *J. Am. Chem. Soc.* 2011, 133, 88-96.

[14] L. Tong, R. P. Thummel *Chem. Sci.* 2016, 7, 6591-6603.

[15] W. Lv, Z. Zhang, K. Yin Zhang, H. Yang, S. Liu, A. Xu, S. Guo, Q. Zhao, *Angew. Chem. Int. Ed.* 2016, 55, 9947-9951.

[16]a) J. S. Nam, M.-G. Kang, J. Kang, S.-Y. Park, S. J. C. Lee, J.-T. Kim, J. K. Seo, O.-H. Kwon, M. H. Lim, H.-W. Rhee, T.-H. Kwon, *J. Am. Chem. Soc.* 2016, 138, 10968-10977; b) S. P-Y. Li, C. T.-S. Lau, M.-W. Louie, Y.-W. Lam, S.-H. Cheng, K. K.-W. Lo, *Biomaterials* 2013, 34, 7519-532.

[17]a) T. N. Singh-Rachford, F. N. Castellano, *Coord. Chem. Rev.* 2010, 254, 2560-2573; b) Y. You, W. Nam, *Chem. Soc. Rev.* 2012, 41, 7061-7084.

[18] W. W. Jianzhang Zhao, Jifu Sun, Song Guo, *Chem. Soc. Rev.* 2013, 42, 5323-5351.

[19]a) G. Li, M. F. Mark, H. Lv, D. W. McCamant, and Richard Eisenberg, *J. Am. Chem. Soc.* 2018, 140, 2575-2586; b) L. Huang, L. Zeng, H. Guo, W. Wu, W. Wu, S. Ji, J. Zhao, *Eur. J. Inorg. Chem.* 2011, 2011, 4527-4533.

[20] S. P.-Y. Li, H.-W. Liu, K. Y. Zhang, K. K.-W. Lo, *Chem.—Eur. J.* 2010, 16, 8329-8339.

[21] R. W. Redmond, I. E. Kochevar, *Photochem. Photobiol.* 2006, 82, 1178-1186.

[22] G. Juan, M. Cavazzoni, G. T. Sáez, J.-E. O'Connor, *Cytometry* 1994, 15, 335-342.

[23] M. Reers, S. T. Smiley, C. Mottola-Hartshorn, A. Chen, M. Lin, L. B. Chen, *Methods Enzymol.* 1995, 260, 406-414.

[24] S. Salvioli, T. L. Pazienza, V. Bobyleva, A. Cossarizza, *Biochemistry (Mosc).* 1998, 63, 235-238.

[25] A. Andreev, A. D. Dupuy, M. Segala, S. Sandugu, D. A. Serra, C. O. Chichester, D. M. Engelman, Y. K. Reshetnyak, *Proc. Natl. Acad. Sci. U.S.A.* 2007, 104, 7893-7898.

[26] S. Luo, X. Tan, Q. Qi, Q. Guo, X. Ran, L. Zhang, E. Zhang, Y. Liang, L. Weng, H. Zheng, T. Cheng, Y. Su, C. Shi, *Biomaterials* 2013, 34, 2244-2251.

[27] S. Xuan, N. Zhao, Z. Zhou, F. R. Fronczek, and M. G. H. Vicente, *J. Med. Chem.* 2016, 59, 2109-2117.

[28]a) E. Zhang, S. Luo, X. Tan, C. Shi, *Biomaterials* 2014, 35, 771-778; b) S. Luo, X. Tan, S. Fang, Y. Wang, T. Liu, X. Wang, Y. Yuan, H. Sun, Q. Qi, C. Shi, *Adv. Funct. Mater.* 2016, 26, 2826-2835; c) S. Luo, E. Zhang, Y. Su, T. Cheng, C. Shi, *Biomaterials* 2011, 32, 7127-7138.

[29] S. Gouthaman, S. Periyaraja, P. Shanmugam, *Tetrahedron Letters,* 2015, 56, 5920-5923.

[30] F. Garces, K. A. King, R. J. Watts, *Inorg. Chem.* 1988, 27, 3464.

[31] J. J. Price, R. F. Schramm, B. B. Wayland, A. Williams, *Inorg. Chem.* 1972, 11, 1280.

[32] K. K.-W. Lo, C.-K. Li, K.-W. Lau, N. Zhu, *Dalton Trans.* 2003, 4682-4689.

[33] C. Bruckmeier, M. W. Lehenmeier, R. Reithmeier, B. Rieger, J. Herranz, C. Kavakli, *Dalton Trans.* 2012, 41, 5026-5037.

[34] M. S. Lowry, W. R. Hudson, R. A. Pascal, Jr., S. Bernhard, *J. Am. Chem. Soc.* 2004, 126, 14129-14135.

[35] M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. J. A. Montgomery, J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O". Farkas, J. B. Foresman, J. V. Ortiz, J. Cioslowski and D. J. Fox, Gaussian 09, Revision B.01, Gaussian Inc., Wallingford, Conn., 2009.

[36] G. M. Sheldrick, *SHELXTL 5.03 (PC-Version), Program Liberary for Structure Solution and Molecular Graphics*; Siemens Analytical Instruments Division: Madison, Wis., USA, 1995.

The invention claimed is:

1. A complex comprising a transition metal and rhodamine tethered bipyridine of Formula I

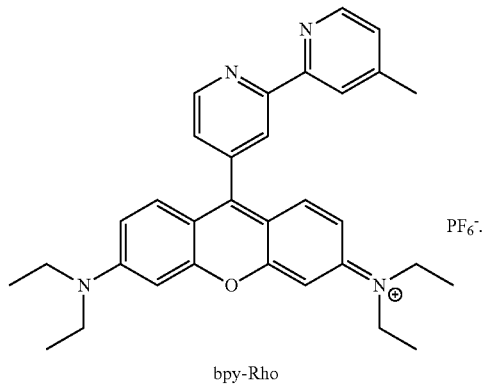

Formula I bpy-Rho

2. The complex according to claim 1, wherein the transition metal is selected from the group consisting of Re(I), Ir(III), Rh(III) and Pt(II).

3. The complex according to claim 1, wherein the complex is selected from the group consisting of:

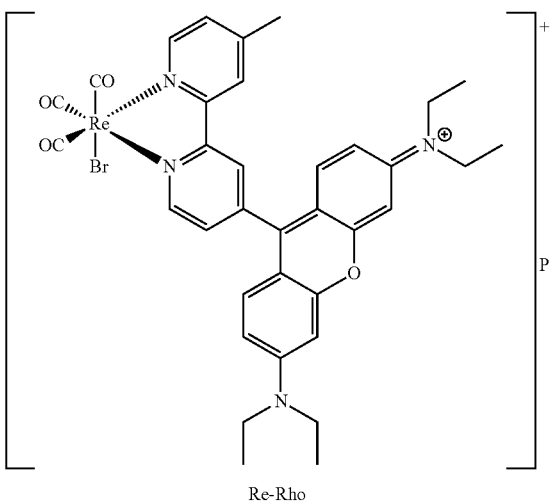

Re-Rho

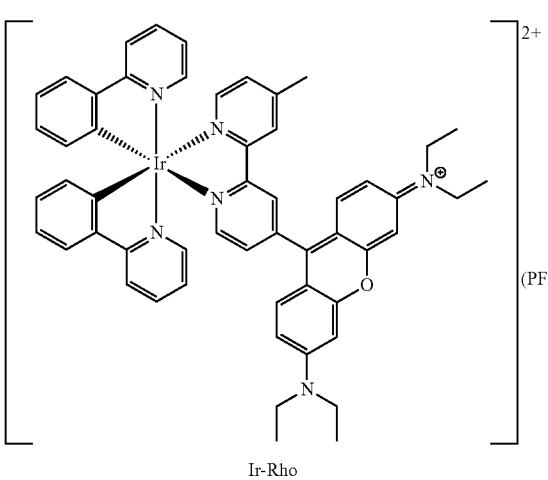

Ir-Rho

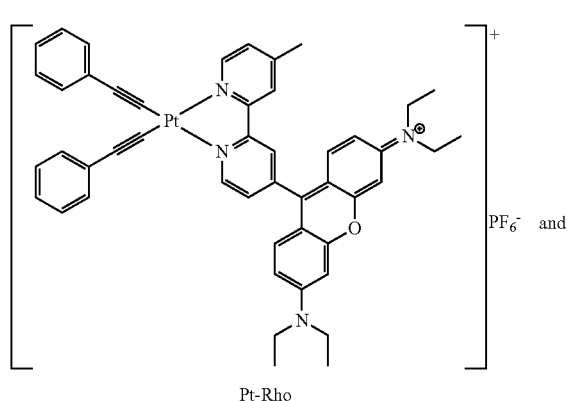

Pt-Rho and

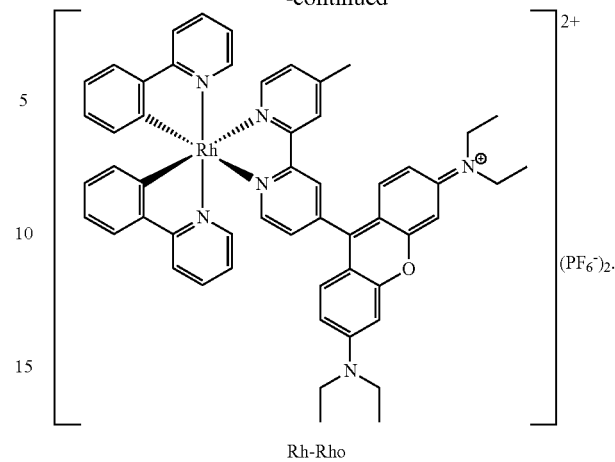

Rh-Rho

4. The preparation method of the complex according to claim 1, comprising:
   (1) preparing bpy-Rho of Formula I according to the following scheme:

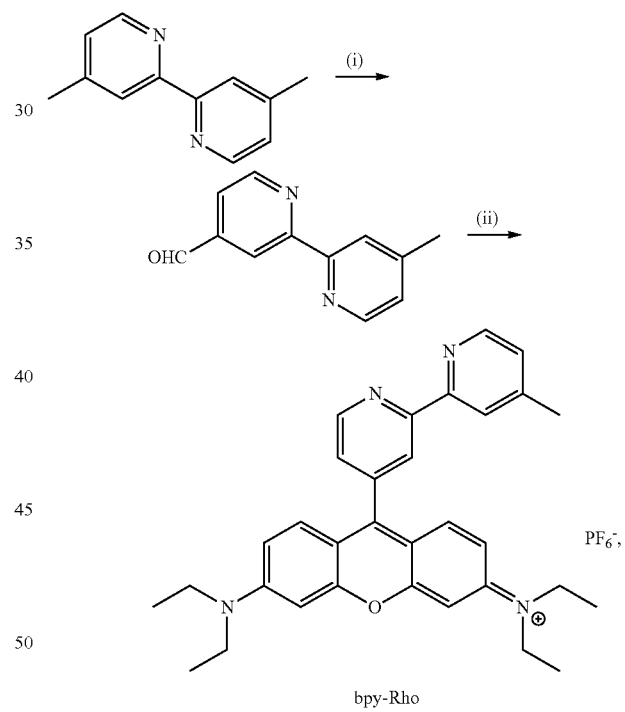

bpy-Rho where (i) conditions are SeO$_2$, 1,4-dioxane, reflux; and
   (ii) conditions are 3-(diethylamino)phenol, CH$_3$COOH, ρ-TsOH, chloranil; and
   (2) preparing the complex by chelating the bpy-Rho with a transition metal.

5. The preparation method according to claim 4, wherein the transition metal is selected from the group consisting of Re(I), Ir(III), Rh(III) and Pt(II).

6. The complex according to claim 1, used as a mitochondria-targeting photosensitizer.

7. The complex according to claim 6, wherein the mitochondria-targeting photosensitizer is used in photodynamic therapy and/or selective tumor cellular uptake.

8. A photodynamic therapy, comprising administrating the complex according to claim 1 to a subject in need thereof.

9. The photodynamic therapy according to claim 8, wherein the complex is selectively uptaken by tumor cells.

* * * * *